US012048557B2

(12) United States Patent
Pratt et al.

(10) Patent No.: US 12,048,557 B2
(45) Date of Patent: *Jul. 30, 2024

(54) SYSTEMS AND METHODS FOR USING WEARABLE COMPUTING DEVICES TO DETECT GESTURES OF PATIENT PRESCRIPTION ADHERENCE

(71) Applicant: Express Scripts Strategic Development, Inc., St. Louis, MO (US)

(72) Inventors: Elizabeth Pratt, Round Rock, TX (US); Michael Lazo, Orlando, FL (US); Alan T. Shutko, St. Louis, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 185 days.

This patent is subject to a terminal disclaimer.

(21) Appl. No.: 17/878,173

(22) Filed: Aug. 1, 2022

(65) Prior Publication Data

US 2022/0361811 A1 Nov. 17, 2022

Related U.S. Application Data

(63) Continuation of application No. 16/731,765, filed on Dec. 31, 2019, now Pat. No. 11,457,861.

(51) Int. Cl.
*G16H 20/10* (2018.01)
*A61B 5/00* (2006.01)
(Continued)

(52) U.S. Cl.
CPC .......... *A61B 5/4833* (2013.01); *A61B 5/0024* (2013.01); *A61B 5/681* (2013.01);
(Continued)

(58) Field of Classification Search
None
See application file for complete search history.

(56) References Cited

U.S. PATENT DOCUMENTS 6,198,383 B1   3/2001   Sekura
7,983,933 B2   7/2011   Karkanias
(Continued)

FOREIGN PATENT DOCUMENTS

EP   3573070 A1   11/2019

OTHER PUBLICATIONS

Chen et al., A Medication Adherence Monitoring System for Pill Bottles Based on a Wearable Sensor, 2014, 36th Annual International Conference of the IEEE Engineering in Medicine and Biology Society, pp. 4983-4986 (Year: 2014).
(Continued)

*Primary Examiner* — Gregory Lultschik
(74) *Attorney, Agent, or Firm* — The Small Patent Law Group

(57) ABSTRACT

A wearable computing device for identifying gestures indicating patient prescription adherence is provided. The wearable computing device includes a processor, a memory, and a motion sensor. The processor is configured to receive a set of prescription plan data defining a prescription for a pharmaceutical associated with a user of the wearable computing device. The processor is also configured to receive a gesture pattern of movement of the wearable computing device. The gesture pattern indicates that a patient is adhering to the prescription. The processor is further configured to detect, with the motion sensor, a first motion pattern associated with the wearable computing device. The processor is also configured to analyze the first motion pattern to determine if the gesture pattern has been performed. Upon determining that the gesture pattern has been performed, the processor is configured to update a prescription usage record.

20 Claims, 17 Drawing Sheets

(51) Int. Cl.
*G16H 10/60* (2018.01)
*G16H 40/63* (2018.01)
*G16H 40/67* (2018.01)

(52) U.S. Cl.
CPC ............ *G16H 10/60* (2018.01); *G16H 20/10* (2018.01); *G16H 40/63* (2018.01); *G16H 40/67* (2018.01); *A61B 2562/0257* (2013.01)

(56) References Cited

U.S. PATENT DOCUMENTS

| | | |
|---|---|---|
| 9,474,481 B2 | 10/2016 | Dagum |
| 9,594,354 B1 | 3/2017 | Kahn |
| 9,760,182 B2 | 9/2017 | Motoyama |
| 9,939,784 B1 | 4/2018 | Berardinelli |
| 9,977,509 B2 | 5/2018 | Park |
| 9,996,109 B2 | 6/2018 | Carceroni |
| 10,022,305 B2 | 7/2018 | Bunker |
| 10,073,666 B2 | 9/2018 | Levesque |
| 10,319,473 B2 | 6/2019 | Fateh |
| 10,365,715 B2 | 7/2019 | Seth |
| 2010/0066763 A1 | 3/2010 | MacDougall |
| 2010/0245131 A1 | 9/2010 | Graumann |
| 2011/0080339 A1 | 4/2011 | Sun |
| 2013/0179188 A1 | 7/2013 | Hyde |
| 2016/0055316 A1 | 2/2016 | Jafari |
| 2016/0136054 A1 | 5/2016 | Bunker |
| 2016/0202665 A1 | 7/2016 | Park |
| 2016/0306932 A1 | 10/2016 | Fateh |
| 2017/0083102 A1 | 3/2017 | Dow |
| 2017/0090557 A1 | 3/2017 | Raffle |
| 2018/0024642 A1 | 1/2018 | Heo |
| 2018/0103901 A1 | 4/2018 | Gandhi |
| 2018/0164892 A1 | 6/2018 | Han |
| 2018/0232054 A1 | 8/2018 | Nair |
| 2018/0261316 A1 | 9/2018 | Spooner |
| 2018/0308571 A1 | 10/2018 | Tupler |
| 2018/0315498 A1 | 11/2018 | Starr |
| 2019/0236465 A1 | 8/2019 | Vleugels |
| 2019/0252053 A1 | 8/2019 | Fateh |
| 2020/0288247 A1 | 9/2020 | Reily |

OTHER PUBLICATIONS

Wang, Chen, et al. "Friend or foe? Your wearable devices reveal your personal pin." Proceedings of the 11th ACM on Asia Conference on Computer and Communications Security. 2016.

SYSTEMS AND METHODS FOR USING WEARABLE COMPUTING DEVICES TO DETECT GESTURES OF PATIENT PRESCRIPTION ADHERENCE

CROSS-REFERENCE TO RELATED APPLICATIONS

This application is a continuation of U.S. patent application Ser. No. 16/731,765 (filed 31 Dec. 2019), the entire contents of which are incorporated herein by reference.

FIELD OF INVENTION

The field relates to systems and methods for monitoring and identifying patient prescription adherence, and more specifically to systems and methods for using wearable computing devices to detect gestures indicating patient prescription adherence.

BACKGROUND OF THE DISCLOSURE

In the context of pharmaceutical, patient adherence quality to prescription plans can have significant ramifications. Generally, a patient may be prescribed a dosage level of a particular pharmaceutical (e.g., a number of pills, a volume of liquid drugs, or a number of inhalations of a gaseous drug) over a particular period of time. Further, in many cases prescriptions entitle a patient to obtain a certain number of refills of the pharmaceutical before the patient is required to obtain a new prescription.

Because pharmaceuticals are often expensive and used in urgent or life-saving care, tracking the usage levels of pharmaceuticals is important to patients, pharmaceutical distributors, and healthcare providers. But, although the prescriptions set forth a defined usage level and rate for pharmaceuticals, in many cases patients do not follow the prescription plan properly. Patients may fail to follow the prescription plan for a variety of reasons including, for example, scheduling difficulties, and discomfort with taking the pharmaceutical, forgetfulness, or misplacement of the pharmaceutical.

When patients fail to take pharmaceuticals at the prescribed rate and dosage, the patients, pharmaceutical distributors, and healthcare providers may all experience adverse consequences. Most importantly, the patient may experience side effects from taking the pharmaceutical at the wrong rate. In some cases, where the pharmaceutical is associated with critical care, a patient may become ill or even die if the pharmaceutical is not taken at the prescribed rate or dosage. Further, if the patient is not taking pharmaceuticals at the appropriate rate, the healthcare provider may have an improper understanding of their patient's care.

Additionally, where a pharmaceutical prescription is associated with a mail-order refill, a patient's failure to adhere to a prescription plan may have adverse impacts. For example, prescription management servers associated with such mail-order refill services presume patient adherence to a prescription plan. Where patients fail to adhere to the prescription plan, the mail-order refill systems may receive improper input and instruct that a patient be sent a refill at an improper time. In such cases, the refill may therefore arrive untimely such that a patient fails to receive the pharmaceutical when needed, or such that the prescription may be wasted.

As such, systems and methods for monitoring prescription adherence are desirable to determine whether a patient is complying with a prescription plan.

BRIEF SUMMARY OF THE INVENTION

In one aspect, a wearable computing device for identifying gestures indicating patient prescription adherence is provided. The wearable computing device includes a processor, a memory, and a motion sensor. The processor is configured to receive a set of prescription plan data. The set of prescription plan data defines a prescription for a pharmaceutical associated with a user of the wearable computing device. The processor is also configured to receive a gesture pattern of movement of the wearable computing device. The gesture pattern indicates that a patient is adhering to the prescription. The processor is further configured to detect, with the motion sensor, a first motion pattern associated with the wearable computing device. The processor is also configured to analyze the first motion pattern to determine if the gesture pattern has been performed. Upon determining that the gesture pattern has been performed, the processor is configured to update a prescription usage record.

In another aspect, a method for identifying gestures of patient prescription adherence is provided. The method is performed by a wearable computing device. The wearable computing device includes a processor, a memory, and a motion sensor. The method includes receiving a set of prescription plan data. The set of prescription plan data defines a prescription for a pharmaceutical associated with a user of the wearable computing device. The method also includes receiving a gesture pattern of movement of the wearable computing device. The gesture pattern indicates that a patient is adhering to the prescription. The method further includes detecting, with the motion sensor, a first motion pattern associated with the wearable computing device. The method also includes analyzing the first motion pattern to determine if the gesture pattern has been performed. Upon determining that the gesture pattern has been performed, the method includes updating a prescription usage record.

In yet another aspect, a prescription adherence system for identifying gestures of prescription adherence performed by a patient is provided. The prescription adherence system includes a prescription management server including a server processor and a server memory. The prescription adherence system also includes a wearable computing device in networked communication with the prescription management server. The wearable computing device includes a device processor, a device memory, and a device motion sensor. The device processor is configured to receive a set of prescription plan data from the prescription management server. The set of prescription plan data defines a prescription for a pharmaceutical associated with a user of the wearable computing device. The device processor is also configured to receive a gesture pattern of movement of the wearable computing device. The gesture pattern indicates that a patient is adhering to the prescription. The device processor is also configured to detect, with the motion sensor, a first motion pattern associated with the wearable computing device. The device processor is also configured to analyze the first motion pattern to determine if the gesture pattern has been performed. Upon determining that the gesture pattern has been performed, the device processor is further configured to update a prescription usage record.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

DETAILED DESCRIPTION

Figure 1:
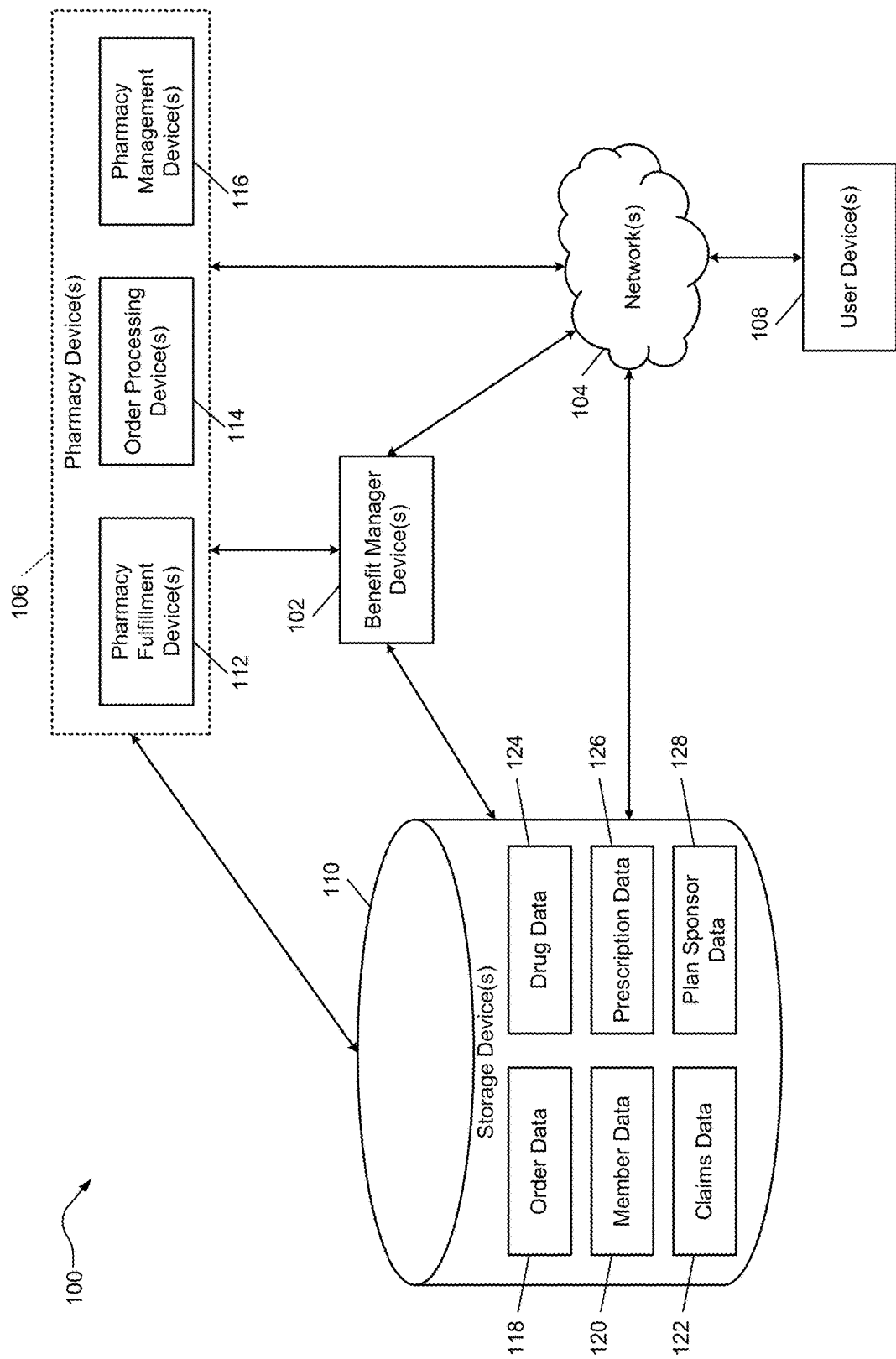
FIG. 1 is a functional block diagram of an example system including a high-volume pharmacy.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

Patient adherence to pharmaceutical prescriptions is a crucial aspect of healthcare delivery. As used herein, when a patient takes pharmaceuticals in a manner consistent with their prescribed use, the patient "adheres" to the prescription or may be said to be "adherent." When patients take pharmaceuticals in a manner inconsistent with their prescriptions, such patients are "not adherent" and may be exposed to risks from under-medication or overmedication, and any associated side effects or consequences. There are a wide variety of reasons that patients may fail to adhere to their prescriptions ranging from a reluctance to take the medication, to discomfort or side effects from the medication to a lack of understanding of the prescription. Further, in some cases, a patient may take a pharmaceutical in a manner that is partially compliant with a prescription, but not entirely. For example, a patient may take a pharmaceutical as prescribed but fail to perform all related steps (e.g., taking the entirety of the medication, drinking fluids, washing hands, or cleaning devices). In such cases, a patient may be "partially adherent" to a prescription if a necessary step was not completed. Because of such risks, reliable means of monitoring and facilitating adherence are desirable.

Patient adherence is also important in the context of high-volume pharmacies or fulfillment centers (for example, a mail order pharmacy, a direct delivery pharmacy, etc.) Such pharmacies or centers depend upon expected patient adherence and usage to determine appropriate times to provide refills. However, as described herein, patient adherence is difficult to predict and may vary significantly across patients. As a result, pharmacies and centers are often lack access to critical data that may be used to process pharmacy refills and fulfillment requests in an appropriate manner. The absence of reliable data regarding adherence makes it difficult or impossible for pharmacies and centers to properly manage inventory and process orders. Additionally, refilling or renewing a prescription at the appropriate time can ensure that the patient has the appropriate supply of the medication available at the correct time. This also assists in maintaining adherence to the drug therapy regimen.

The systems and methods described address these problems by providing a prescription adherence system including a wearable computing device configured to define, monitor, and detect prescription adherence, and to provide improved adherence data to prescription management servers and other systems. Specifically, the wearable computing devices described herein are configured to detect motion patterns of users that indicate that the user is adhering to one or multiple prescriptions. In one example, the wearable computing device is configured to be trained by a user to identify specific motion patterns as matching gesture patterns (or "gestures") that the user may make when adhering to a given prescription. A gesture can be the movement of the wearable device in three-dimensional space and can include multiple measurable factors, e.g., distance, speed, acceleration, repetitions, rotation, and the like. The wearable computing device is configured to detect such gestures from a first motion pattern when a user is adhering to a particular prescription. In some examples, the wearable computing device may detect gestures without training, based on predefined motion patterns. Such motion patterns may be based on a motion model determined remotely and downloaded to a user device. By providing adherence monitoring through the use of the wearable computing devices based on device training, the systems and methods described provide a solution to the problem of patient adherence wherein that solution is necessarily rooted in computing technology.

In the example embodiment, the wearable computing device is a "smart watch" including, for example, an Apple Watch, a Samsung Smartwatch, or any other known smart watches capable of functioning in the manner described herein. The wearable computing device includes a touchscreen graphical display configured to provide graphical user interfaces and receive user inputs. The wearable computing device may further be configured to receive audio input through an interface such as a microphone, and to present audio output through a speaker. The wearable computing device is additionally configured to communicate directly or indirectly with external devices including but not limited to the prescription management server and other user computing devices. In the example embodiment, the wearable computing device includes a communications interface configured to provide wireless communication to such devices. The wearable computing device may utilize any suitable wireless protocol for communications including but not limited to cellular communications, Bluetooth® connectivity, WiFi, near field communication (NFC), and Zigbee. In some examples, the wearable computing device is also configured to communicate through wired networking protocols.

As described herein, the wearable computing device includes at least one sensor capable of detecting motion, location, and orientation ("motion sensor") and is configured to detect motion and location attributes of the wearable computing device over time. The motion sensors may include, for example, a three-axis gyroscope, an accelerometer, a step counter, and a GPS sensor. The attributes detected by the motion sensor(s) include: (a) the orientation of the wearable computing device using a suitable motion sensor (e.g., a gyroscope); (b) the speed and acceleration of the wearable computing device using a suitable motion sensor (e.g., an accelerometer); (c) the absolute and relative location of a user using a suitable motion sensor or sensors (e.g., one or a combination of an accelerometer, a GPS sensor, or location services); and (d) physical steps taken by the user using a suitable motion sensor (e.g., a step counter). Additionally, the wearable computing device may be configured to include additional environmental sensors that may track environmental conditions (e.g., temperature, pressure, and humidity) and biometric sensors that may track user biometrics (e.g., pulse or heart rate, hydration level, oxygen level, and glucose levels). The motion sensors of the wearable computing device are capable of tracking motion and changes of orientation at fine-grained levels so that user location changes can be determined at the level of millimeters or sub-millimeters and motion can be tracked at fractions of a second. The motion sensors are also capable of tracking subtle changes in orientation (using, for example, a three-axis gyroscope) at the level of hundredths of degrees over each of three spatial axes. In the example embodiment, the wearable computing device has motion sensors capable of detecting location, motion, orientation, and orientation changes at such levels of specificity. The wearable computing device also includes components to manipulate signals detected by the motion sensors (and other sensors) to generate data output that can be processed by the software described herein. In the example embodiment, such manipulation is performed by signal conditioning units. In other examples, any suitable component may be used. The motion sensors of the wearable computing device are capable of tracking and monitoring user motion at great levels of specificity. In examples, motion sensors in wearable computing device can detect the motion of a user hand to detect keystrokes on a keypad. Further, in many examples, wearable computing device is "oriented" or "trained" by a user to better detect user motion and orientation. For example, in the systems and methods described herein, the wearable computing device may track the motion of the hand of a user toward the user's face when a patient consumes a pharmaceutical orally. In some examples, the wearable computing device is calibrated by the user to define: (a) changes in the orientation and location of the wearable computing device as the user moves the wearable computing device to different parts of the body of the user; (b) changes in the orientation and location of the wearable computing device as the user performs various actions such as opening and closing containers, filling vessels and syringes, applying pharmaceuticals to the skin, applying pharmaceuticals within body cavities; dispensing vessels and syringes; and using devices such as nebulizers and inhalers; and (c) collective movements (changes in orientation and location) when a user adheres to a prescription as a gesture pattern or ("gesture") conforming to a model.

The wearable computing device is also configured to selectively monitor for motion patterns (or motions) during periods of time that the user is expected to adhere to a particular prescription. Specifically, the wearable computing devices may obtain information related to prescription adherence timing and identify windows of time in which adherence is anticipated. By selectively monitoring at such times, the methods described reduce power consumption and prolong the battery life of wearable computing devices. As a result, the systems and methods described solve a technical problem of power consumption during motion monitoring with a solution necessarily rooted in computing technology: selective monitoring for gestures of prescription adherence based on predicted adherence windows to provide longer battery life.

The wearable computing device is also configured to track the usage and inventory level of a particular prescription pharmaceutical, and to facilitate the refilling of the prescription pharmaceutical through communication with other devices including a prescription management server. By using the wearable computing device to track each motion pattern in order to identify each gesture indicating prescription adherence, and confirming such adherence, the systems and methods also provide accurate and current data regarding patient adherence to prescription management servers used to track prescription status and adherence. Thereby, the systems and methods improve inventory management and can be used to provide timely order processing by accurately identifying gestures of patient adherence and using the captured information to determine when refills or renewals may be needed. In some embodiments, the systems and methods described allow for a patient to make direct requests for refills of pharmaceuticals or prescription renewals. As such, embodiments of the systems and methods described address a technological problem in pharmacies and fulfillment centers by addressing unavailability of accurate information on patient adherence to prescriptions.

Embodiments of the systems and methods described solve these problems by employing a technological solution of detecting and confirming patient adherence using a wearable computing device to capture motions and detect gestures, and relaying monitored information to computing systems including prescription management servers used to process and fulfill prescription orders. Further, the systems and methods described employ wearable computing devices that allow monitoring and detecting of patient adherence in a variety of contexts.

The systems and methods described also address a related problem of alerting caregivers and healthcare providers of prescription adherence by a patient. For example, in some embodiments the wearable computing device is capable of notifying other computing systems that a patient has made a gesture indicating prescription adherence and/or confirmed prescription adherence. These embodiments address a problem for caregivers and healthcare providers lacking timely access to prescription adherence data. By providing such notifications, these embodiments reduce the challenges of such caregivers and healthcare providers monitoring and ensuring adherence compliance.

In the example embodiment, a wearable computing device is used to identify gestures of prescription adherence. The wearable computing device includes at least a processor, a memory, and a motion sensor. The wearable computing device may also include other necessary components including an input/output component, a communications interface, other sensors, power and battery management components, and security components. The processor is configured to perform the steps described herein. The wearable computing device is configured to execute software to: (a) receive prescription plan data; (b) define "gestures" associated with patient prescription adherence for the prescription plan data; (c) track and monitor gestures indicating prescription adherence based on the defined (or trained) gestures or pre-defined default gestures for the prescription plans of the prescription plan data; (d) determine windows of expected prescription adherence; (e) selectively track and monitor for gestures during the determined windows of expected prescription adherence; (f) confirm patient prescription adherence after the detection of gestures; (g) configure the software based on user input; (h) provide user interfaces for refills of pharmaceuticals and prescription renewals; and (i) facilitate communication regarding prescription adherence to other computing devices including devices used by health care providers or caregivers. In some examples, the software is encoded onto the memory and executed by the processor. In other examples, the software is downloaded from a computer system in networked communication with the wearable computing device and stored into memory and/or executed by the processor.

In the example embodiment, the wearable computing device receives a set of prescription plan data defining a prescription for a pharmaceutical associated with a user of the wearable computing device. Prescription plan data may be stored in a system including the wearable computing device, the prescription management server, or any other suitable device. Prescription plan data further relates a particular user to the prescriptions prescribed to that user. In some examples, the prescription plan data is stored in a user profile on the prescription management server. The set of prescription plan data includes information related to the prescription including, for example: (a) the name or identifier of the prescription; (b) the type of prescription (i.e., the type of prescription medication and the method of administration); (c) the prescribed rate of administration of the pharmaceutical; (d) the historical record of adherence to the prescription; (e) steps required for administration; and (f) prescription usage history including availability of prescriptions with the patient and availability of prescription refills. In some examples, the software allows the user to request the prescription plan data from an external networked computing device such as a prescription management server. In further examples, the software prompts the user to provide credentials and authentication before the set of prescription plan data is transmitted. In some examples, the user is prescribed with multiple pharmaceuticals and the set of prescription plan data transmitted to the wearable computing device may include data defining multiple prescriptions for multiple pharmaceuticals. In further examples, the systems and methods are configured to protect patient healthcare data. In such examples, the wearable computing device does not present the name or type of any prescription or prescribed pharmaceutical to any third-party. Instead, the systems and methods allow the user to configure the display of the wearable computing device so that such information is not discernible to a third-party. In one example, the wearable computing device can be configured through a user interface available on the wearable computing device. The user interface allows the user to select a pseudonym, alternate identifier, or a color code to obscure such information. In a second example, a user may use a second computing device (such as a mobile computing device or a laptop computer) in communication with the wearable computing device. In such an example, the second computing device is configured to run software that configures the software of the wearable computing device.

The mobile computing device also receives a gesture pattern of movement of the wearable computing device. As described herein, the gesture pattern is a model that indicates that a patient is adhering to the prescription. The gesture pattern may be defined based on pre-defined defaults or based on training from the user using the software. The gesture pattern may be defined in a training mode as follows. The wearable computing device provides a user interface to the software that allows a user to select a training option for a prescription. (Where the set of prescription plan data is associated with multiple prescriptions, the user interface provides a selection option to allow a user to select a particular prescription on which to train.) Based on the set of prescription plan data, the software causes the user to prompt the user with displayed instructions to perform each step of the prescription. As the user performs each step of the prescription, the wearable computing device tracks (or captures) sensor data (or motion data) from the movement sensors, processes such information into movement information using motion processing algorithms, and stores sensor data and movement information. In some examples, the wearable computing device is configured to require completion of a minimum number of cycles (or iterations or passes) of prescription adherence before the wearable computing device (and software) is trained. In such examples, after the user completes all the steps of the prescription, the wearable computing device counts (or iterates) the number of training cycles completed. Until the threshold is met, the wearable computing device and software prompts the user to repeat the steps of the prescription. The threshold minimum number of cycles may be pre-defined in the software or in the set of prescription plan data. The threshold minimum number of cycles may vary based on prescription type. For example, prescriptions involving subtler (or smaller) motion may require more training cycles than prescriptions involving large motions. In some examples, the software and wearable computing device may not capture all of the motion information required for a particular training cycle. In such examples, the software and wearable computing device may determine that a training cycle did not successfully complete (or did not complete within a minimum time threshold) and prompts the user to repeat a training cycle. When the minimum number of training cycles are completed, the wearable computing device processes the sensor data from each cycles to define a gesture pattern on which future adherence may be tracked. In some examples, the software and wearable computing device creates ranges of motion values and times associated with each of the steps of the prescription. The ranges may be defined based on statistical processing by, for example, finding motion values and times within certain percentiles of the captured training data or within a certain range from the median or mean of the training data. In other examples, outlier data may be excluded from the training data for the purposes of defining gesture patterns.

In embodiments where the gesture pattern is defined based on pre-defined defaults, such pre-defined defaults are created based on input from training cycles completed by previous users using a wearable computing device for a variety of prescriptions.

The following briefly describes the categories of prescriptions for which adherence may be detected using the wearable computing device and the systems and methods described herein. Patients may be prescribed prescription pharmaceuticals that can be administered in several ways including at least the following: (a) oral ingestion of a solid pharmaceutical (in any suitable form including capsule, tablet, chewable tablet, or powdered); (b) intravenous injection using a syringe administered in any suitable manner including intramuscularly (into a muscle), intravenously (into a vein), intrathecally (into a location near the spinal cord), or subcutaneous (under the skin); (c) ingestion of pharmaceutical sublingually (where a pharmaceutical is placed under the tongue) or buccally (where a pharmaceutical is placed between the gums and the cheek of the mouth); (d) application into a body cavity for vaginal or rectal administration; (e) placement of a pharmaceutical into the eye (via the ocular route) or the ear (via the otic route); (f) nasal spray into the nose wherein the pharmaceutical is absorbed through the nasal membrane; (g) breathing the pharmaceutical in through the lungs after administration via an inhaler (administered through the mouth) or a nebulizer (administered through the mouth or nose); (h) application of the pharmaceutical on the skin for topical (local) administration or systemic (bodywide) administration; or (i) transdermally using a suitable delivery vehicle such as a patch. As explained below, the wearable computing device is capable of detecting and monitoring adherence for prescriptions of these and similar types. Further, for each of these types of prescriptions, the wearable computing device may be trained and may prompt the user to complete necessary training cycles. Exemplary motions made for each of these types of prescriptions are described below.

For example, a patient taking a capsule or a tablet for oral ingestion is required to dispense the pharmaceutical from, for example, a pill bottle or another suitable container (e.g., a pill box) and consume the pharmaceutical. To do this, in an example embodiment, the patient performs certain steps including at least some of the following: (a) obtaining the container containing the pharmaceutical; (b) opening the container (e.g., removing caps from pill bottles through rotation or pushing a pill case open); (c) dispensing the pharmaceutical into an open hand of the patient (e.g., by shaking the container with the other hand or retrieving a pharmaceutical from the container with the other hand); (d) bringing the hand with the pharmaceutical to the mouth of the patient; and (e) ingesting the pharmaceutical. In some cases, the patient may subsequently obtain a cup of water (or food) and ingest it. During each of these steps, the patient makes corresponding body motions as part of the steps. As such, when the wearable computing device is in a training mode, the wearable computing device prompts a user to perform some or all of the steps above along with any other necessary steps for a particular prescription. Once sufficient training cycles are completed, the gesture pattern is defined for this type of prescription and the motions for the prescription can be tracked and monitored.

Likewise, when a patient uses a syringe to inject a pharmaceutical, the patient performs steps including at least some of the following: (a) retrieving a sanitizing tool such as an alcohol tissue; (b) applying the sanitizing tool to an injection site; (c) retrieving a syringe; (d) retrieving the fluid containing the pharmaceutical (typically stored in a bottle or another container from which the syringe may withdraw); (e) loading the syringe (e.g., by withdrawing an appropriate fluid volume from a bottle); (f) verifying the level volume of the prescription by holding the syringe at eye level; (g) clearing the syringe of air; (h) placement of the syringe at the appropriate injection site (e.g., near a vein on the arm or leg, at the abdomen, or at or near the lower back); (i) injection of the pharmaceutical into the injection site; (j) removing the syringe from the injection site; and (k) disposal of the syringe into an appropriate container for syringes or sharps. In an example, some patients tap the syringe or tap the syringe a certain number of times (e.g., once, twice, three times or more) during the step (g) clearing air from the syringe, this may be a unique identifying step to determine whether the user has administered the injection. During each of these steps, the patient makes corresponding body motions as part of the steps. As such, as in the examples above, the wearable computing device in a training mode prompts a user to perform some or all of the steps above along with any other necessary steps for a particular prescription. Once sufficient training cycles are completed, the gesture pattern is defined for this type of prescription and the motions for the prescription can be tracked and monitored.

When a patient takes a pharmaceutical sublingually or bucally, the patient performs steps including at least some of the following: (a) obtaining the container containing the pharmaceutical (typically a film, dissolving capsule, pill, or pouch); (b) opening the container; (c) retrieving the pharmaceutical into a hand of the patient; (d) bringing the hand of the patient with the pharmaceutical towards the mouth and towards the bottom of the tongue or the gums; (e) placing the pharmaceutical sublingually or bucally; and (f) moving the applying hand away from the mouth. During each of these steps, the patient makes corresponding body motions as part of the steps. As such, as in the examples above, the wearable computing device in a training mode prompts a user to perform some or all of the steps above along with any other necessary steps for a particular prescription. Once sufficient training cycles are completed, the gesture pattern is defined for this type of prescription and the motions for the prescription can be tracked and monitored.

When a patient takes a pharmaceutical through insertion into a body cavity, the patient performs steps including at least some of the following: (a) obtaining the container containing the pharmaceutical (typically a suppository in the case of a rectal cavity and a solution, tablet, cream, gel, suppository, or ring in the case of a vaginal cavity); (b) opening the container; (c) dispensing the pharmaceutical into a hand of the patient; (d) positioning the patient's hand with respect to the body cavity for insertion; (e) inserting the pharmaceutical into the body cavity using the patient's hand; and (f) moving the hand away from the body cavity. Additional steps that can be sensed by the wearable device is the movements after step (f), e.g., how user disposes of the wrapping, packaging, etc. Some users may dispose before insertion. Other uses may dispose after insertion. An additional steps is handwashing. Individuals will wash their hands with different motions and for different time periods. These can also be part of the motion tracking. During each of these steps, the patient makes corresponding body motions as part of the steps. As such, as in the examples above, the wearable computing device in a training mode prompts a user to perform some or all of the steps above along with any other necessary steps for a particular prescription. Once sufficient training cycles are completed, the gesture pattern is defined for this type of prescription and the motions for the prescription can be tracked and monitored.

When a patient takes a pharmaceutical through placement into the eye or ear, the patient performs steps including at least some of the following: (a) obtaining the container containing the pharmaceutical (typically a liquid, gel, or ointment); (b) opening the container; (c) dispensing the pharmaceutical into the hand of the patient (in some cases, an applicator is used to apply the pharmaceutical and the patient obtains the applicator and dispenses the pharmaceutical to the applicator); (d) positioning the pharmaceutical or the applicator at or near the eye or ear; (e) applying the prescription to the eye or ear; and (f) moving the applying hand (and the applicator, if any) away from the eye or ear. During each of these steps, the patient makes corresponding body motions as part of the steps. As such, as in the examples above, the wearable computing device in a training mode prompts a user to perform some or all of the steps above along with any other necessary steps for a particular prescription. Once sufficient training cycles are completed, the gesture pattern is defined for this type of prescription and the motions for the prescription can be tracked and monitored.

When a patient takes a pharmaceutical using a nasal spray, the patient performs steps including at least some of the following: (a) obtaining the applicator containing the nasal spray; (b) positioning the nasal spray inside a nostril; (c) applying the nasal spray as directed (in many cases, the patient will move the nasal spray to the other nostril and apply it there by squeezing the spray); and (d) moving the nasal spray away from the nose of the patient. During each of these steps, the patient makes corresponding body motions as part of the steps. As such, as in the examples above, the wearable computing device in a training mode prompts a user to perform some or all of the steps above along with any other necessary steps for a particular prescription. Once sufficient training cycles are completed, the gesture pattern is defined for this type of prescription and the motions for the prescription can be tracked and monitored.

When a patient takes a pharmaceutical using an inhaler, the patient performs steps including at least some of the following: (a) obtaining the inhaler; (b) removing the cap of the inhaler; (c) if the inhaler is single use, obtaining and loading a capsule into the inhaler; (d) position the inhaler in front of the patient's face; (e) in some cases, shake or jiggle the inhaler; (f) put the mouthpiece of the inhaler between the lips of the patient; (g) depress the top of the inhaler to release the pharmaceutical (typically with an index finger); and (h) remove the inhaler from the mouth. During each of these steps, the patient makes corresponding body motions as part of the steps. As such, as in the examples above, the wearable computing device in a training mode prompts a user to perform some or all of the steps above along with any other necessary steps for a particular prescription. Once sufficient training cycles are completed, the gesture pattern is defined for this type of prescription and the motions for the prescription can be tracked and monitored.

When a patient takes a pharmaceutical using a nebulizer, the patient performs steps including at least some of the following: (a) connecting the hose of the nebulizer to an air compressor; (b) obtain a medicine receptacle; (c) obtain a prescription pharmaceutical and open the same; (d) dispense the prescription pharmaceutical into the medicine receptacle according to the prescription; (e) attach the hose and mouthpiece to the filled medicine receptacle; (f) hold the mouthpiece in a hand of the patient; (g) move the hand with the mouthpiece to the face of the patient and, if necessary, secure the mouthpiece with a strap or band; (h) push a button or switch to activate the nebulizer; (i) push a button or switch to deactivate the nebulizer when completed; (j) remove the mouthpiece from the face of the patient and, if necessary, remove the strap or band; (k) disconnect the hose from the compressor; and (l) clean the components of the nebulizer as needed. During each of these steps, the patient makes corresponding body motions as part of the steps. As such, as in the examples above, the wearable computing device in a training mode prompts a user to perform some or all of the steps above along with any other necessary steps for a particular prescription. Once sufficient training cycles are completed, the gesture pattern is defined for this type of prescription and the motions for the prescription can be tracked and monitored.

When a patient takes a pharmaceutical using a topical application, the patient performs steps including at least some of the following: (a) obtaining the container containing the pharmaceutical (typically a gel, cream, or ointment); (b) opening the container; (c) dispensing the pharmaceutical into the hand of the patient; (d) moving the hand to a recommended or prescribed area of the patient's body; (e) applying the prescription to skin of the patient in any suitable manner; and (f) removing the hand from the skin. When a patient takes a pharmaceutical using a systemic application, the patient performs the same steps but may apply the prescription to several areas. During each of these steps, the patient makes corresponding body motions as part of the steps. As such, as in the examples above, the wearable computing device in a training mode prompts a user to perform some or all of the steps above along with any other necessary steps for a particular prescription. Once sufficient training cycles are completed, the gesture pattern is defined for this type of prescription and the motions for the prescription can be tracked and monitored.

When a patient takes a pharmaceutical using a transdermal pharmaceutical, the patient performs steps including at least some of the following: (a) obtaining the container containing the pharmaceutical (typically a patch); (b) opening the container; (c) dispensing the pharmaceutical into the hand of the patient; (d) removing any covering or sheathing on the pharmaceutical to ensure it will function and adhere to the skin of the patient; (e) moving the hand to a recommended or prescribed area of the patient's body; (f) applying the prescription to skin of the patient in any suitable manner; and (g) removing the hand from the skin. During each of these steps, the patient makes corresponding body motions as part of the steps. As such, as in the examples above, the wearable computing device in a training mode prompts a user to perform some or all of the steps above along with any other necessary steps for a particular prescription. Once sufficient training cycles are completed, the gesture pattern is defined for this type of prescription, stored as gesture patterns (or gesture models), and motion patterns for prescription adherence can be tracked and monitored by applying the model for gesture patterns.

In some examples, additional steps may be performed as appropriate to the prescription, the pharmaceutical, and the packaging and equipment associated with the pharmaceutical. For example, some pharmaceuticals are stored in blister packs and a patient may need to remove the pharmaceutical from the blister pack. Further, in many examples a syringe has a safety cap that is removed prior to use. Additionally, in many cases patients may wash their hands before taking any prescription. Where required, such additional steps may be used to define a gesture pattern, used to prompt a user in training mode, and detected for in analyzing whether motion patterns match gesture patterns.

An additional steps that can be sensed by the wearable device and trained to detect medication and user operation can relate to disposing of packaging or used applicators. For example, a user may use a highly specific sequence of steps during taking of the medicine. The packaging may be thrown away before application, during the steps described above with each medicine type, or after the medicine is taken. The wearable device can also sense post medicine movement that may be part of a user's process for taking their medicine. For example, a user washes their hands after taking their medicine. The washing motions may be individualized to the user. Each user may use a unique gesture pattern when washing their hands. This gesture pattern can be used to confirm taking the medicine. A user may also perform a motion of which they are not aware is part of their movement profile when taking their medicine. For example, the user may routine or always place both hands on their counter or table after taking their medicine or place both hands at their sides. Another motion is the user supporting their weight on their hands and leaning toward their mirror in a bathroom. These motions can be part of an individual user's gesture pattern, such after medicine adherence activity can be learned and used to more confidently track adherence. In operation, the device may ask the user if it may track user activity, e.g., wearable device movement for tens of seconds, a minute, two minutes or more after taking the medicine. The device can then learn additional patient gestures to add to that patient's gesture profile.

Based on the gesture patterns defined by the training cycles described above, or based on pre-defined defaults, the wearable computing device detects, with the motion sensor (s), a first motion pattern associated with the wearable computing device. The first motion pattern may, as explained in detail above, include a variety of motions. As such, the wearable computing device may capture multiple motions based on the definitions of prescription adherence set in the prescription plan data or otherwise.

To minimize the use of the battery of the wearable computing device, in some examples the wearable computing device selectively detects (or monitors) for motion patterns during times in which prescription adherence is expected. Specifically, the wearable computing device may identify "windows" in which adherence is expected based on one or a combination of: (a) prescription rate information as indicated by the set of prescription plan data; (b) past gestures detected by the wearable computing device for a particular prescription; (c) past confirmations of adherence provided by a user at the user interface of the software; and (d) input provided by a user regarding normal or expected windows of prescription adherence. Specifically, the set of prescription plan data typically defines a frequency of prescription of a particular pharmaceutical. Further, as explained herein, the wearable computing device actively tracks and monitors for motion patterns that match gesture patterns and may (in some examples) confirm adherence based on detection of such gestures. (When a motion matching a gesture pattern is detected, the user interface may prompt a user to confirm that prescription adherence occurred.) Further, the software may allow a user to configure (whether in the wearable computing device or on a separate computing device such as a mobile computing device) typical periods of adherence for each prescription. In such examples where detection is selective, the wearable computing device processes such information to define windows of expected adherence and monitors for motion patterns during such windows (or identified periods of time) of expected adherence. Through such selective monitoring and tracking, the wearable computing device avoids excess usage of the motion sensor, system resources, and the battery.

In some examples, the software (or wearable app) tracks adherence to multiple prescriptions and the user may navigate to select interfaces associated with a particular prescription. Where multiple prescriptions are tracked and have overlapping "windows", the user may provide input to indicate when they are adhering to a particular prescription.

The wearable computing device is also configured to analyze the first motion pattern to determine if a gesture pattern has been performed (i.e., that the first motion pattern matches the gesture pattern). Specifically, the wearable computing device processes the sensor data associated with the first motion pattern and compares that processed sensor data to the gesture data defined by training or pre-defined in defaults. (Note that the pre-defined defaults are typically set by training by other prior users.) In the example embodiment, the gesture pattern is defined as a set of threshold motion and/or location values arranged in a sequenced manner and arranged with corresponding expected timing. Accordingly, software receives motion, location, and orientation values associated with the first motion pattern from the motion sensors of the wearable computing device (and the signal conditioning unit, if any) and compares such values to the values of the gesture pattern. If the detected values of the first motion pattern correspond to the values of the gesture pattern, the software determines that the gesture pattern has been performed by the user (or patient), indicating that the patient has adhered to the prescription.

In most cases, prescription is also required within a time period determined by the prescribed rate and the past adherence. For example, if a patient is required to administer a prescription every four hours and last took a prescription at noon, the patient should administer the next prescription at approximately 4:00 PM. As such, the software may define a window within which adherence is expected by the prescription. As described above, in some examples, the wearable computing device is configured to selectively monitor for motion patterns within the window. In such examples, when the user fails to provide the first motion pattern within the window, the software is configured to send an alert to the user interface indicating that a prescription adherence gesture was not made within the expected window. The software is also configured to update a prescription usage record locally with an update reflecting that adherence was not received in the window. In some examples, the software is configured to transmit an update to the prescription management server or to third-party computing devices used by a healthcare provider or a guardian. The software also causes the user interface to display a retry option to a user that, when selected, allows a user to indicate that they are going to adhere to the prescription. When the retry option is selected, the wearable computing device monitors for a first motion pattern and, if so detected, analyzes the first motion pattern to determine if a gesture corresponding to the first gesture pattern has been provided.

In other words, upon determining that the gesture pattern has been performed (i.e., that the first motion pattern matched the gesture pattern for the prescription), the wearable computing device updates a prescription usage record. The prescription usage record may be stored and updated locally at the wearable computing device including at its memory. The prescription usage record may also be stored at the prescription management server and updated there by the wearable computing device transmitting an update message to the prescription management server. The prescription usage record may alternately be stored in a separate server such as a database server, or any combination of the foregoing.

As described above, the wearable computing device includes software that may be used to train the wearable computing device and its software to detect motion patterns as matching gesture patterns, and thereby indicating gestures of prescription adherence have been performed. The wearable computing device is configured to determine that the wearable computing device is in a training mode to define the gesture pattern. In the example embodiment, the user interface of the software allows a user to initiate training by selecting a training option through any suitable input including selecting an icon, making a voice command to a speaker, making a motion indicative of training initiation, or any other suitable means. When the wearable computing device determines that it is in training mode, it is configured to detect, with the motion sensor, a training motion pattern associated with the wearable computing device and define the gesture pattern based on the training motion pattern. More specifically, as described above, the wearable computing device receives sensor data from the user performing training motion patterns related to prescription adherence during the training period. In some cases, the user interface may prompt the user to perform each, or all of the motions of the training motion patterns as reflected above, and appropriately distinguished for each type of prescription. The user interface may also indicate when a user has failed to perform some or all of a training motion pattern, and to restart the training if appropriate sensor data was not captured. The wearable computing device processes the sensor data to define a gesture pattern, as described above, based on the data received from the training cycles.

The wearable computing device and software are also configured to facilitate prescription refills and renewals by: (a) monitoring the level of prescriptions available to a patient (or user) based on inventory information received from the prescription management server and usage data determined based on detected gestures of prescription adherence; (b) providing user interfaces to allow a user to request a refill of a prescription when an associated inventory level falls below a minimum threshold (typically set based on the expected delivery time of the refill and amount of prescription a user requires during the expected delivery time, based on the prescription plan data); and (c) providing user interfaces to allow a user to initiate a request for a prescription renewal when no more prescription refills are available and the associated inventory level falls below a minimum threshold (typically set based on the expected prescription renewal time and the amount of prescription a user requires during the expected prescription renewal time). Specifically, the wearable computing device receives the set of prescription plan data and the prescription usage record reflecting the patient prescription usage, including usage determined based on detected prescription adherence gestures. The wearable computing device processes the prescription usage record and the set of prescription plan data to determine an inventory level associated with the prescription. The wearable computing device determines whether the inventory level has fallen below a minimal threshold for prescription refills (defined as specified above) and presents the user with a refill user interface to request a refill of the prescription. If the wearable computing device receives a refill request from the refill user interface, the wearable computing device transmits a refill order to a suitable system such as the prescription management server. In some cases, the wearable computing device determines that the user must authenticate themselves after receiving a refill request and before transmitting a refill order. Such authentication may be performed in any suitable manner including providing a password or a personal identification number, performing a two-factor authentication, providing a biometric input such as a thumbprint, or providing suitable credentials on a second device such as a mobile computing device running software corresponding to the software of the wearable computing device and associated with the same user account. After the refill order is transmitted, external systems such as the prescription management server process the refill order and provide the refill to the user.

Similarly, the wearable computing device determines whether the inventory level has fallen below a minimal threshold for prescription renewals (defined as specified above when the inventory level falls below a minimal amount and no prescription refills are available to the user) and presents the user with a renewal user interface to request a renewal of the prescription. If the wearable computing device receives a renewal request from the renewal user interface, the wearable computing device transmits an initiation for a renewal process to a suitable system such as the prescription management server. Again, in some cases, the wearable computing device determines that the user must authenticate themselves after receiving a renewal request and before transmitting the initiation for the renewal process. Such authentication may be performed in any suitable manner including providing a password or a personal identification number, performing a two-factor authentication, providing a biometric input such as a thumbprint, or providing suitable credentials on a second device such as a mobile computing device running software corresponding to the software of the wearable computing device and associated with the same user account. After the initiation is transmitted, external systems such as the prescription management server process the initiation and the patient (or user), and an associated healthcare provider have any necessary contact before a renewal is provided to the user.

As described above, the wearable computing device may be configured to present the user with a confirmation user interface to confirm adherence to the prescription. Specifically, in some examples if the wearable computing device determines that the first motion pattern matches a gesture pattern, the wearable computing device may seek confirmation from the user. The wearable computing device may provide the confirmation user interface in any suitable manner including: (a) a visual or audio prompt for the user to provide a confirming input at a touchscreen; (b) a visual or audio prompt for the user to provide an audio input at a microphone; or (c) a visual or audio prompt for the user to perform a confirmatory motion indicating confirmation. Upon receiving a confirmation at the confirmation interface, the wearable computing device is configured to update the prescription usage record.

As described above, in some examples the wearable computing device is configured to selectively monitor for the first motion pattern during windows in which adherence is expected. In other examples, the wearable computing device may selectively monitor for the first motion pattern when the user is known to be near a prescription pharmaceutical or any containers associated with the prescription pharmaceutical. Such containers may include boxes and bottles containing the prescription pharmaceutical or associated apparatus such as syringes, applicators, nebulizers, and inhalers. In the example embodiment, such containers include communications interfaces that can be detected wirelessly by the wearable computing device. Such communications interfaces may use any suitable communications protocol such as Bluetooth®, WiFi, near field communication (NFC), and Zigbee. The wearable computing device may be configured to communicate with such communications interfaces and receive a proximity signal from the communications interface. The proximity signal may directly or indirectly indicate how far apart the communications interface and a party receiving the signal are. For example, the party receiving the signal (here, the wearable computing device) may be able to determine distance based on location data associated with the communications interface of the container and the sensors of the wearable computer device. Alternately, the wearable computing device may determine the distance between the device and the container based on, for example, signal strength. The wearable computing device receives such a proximity signal from a communication interface associated with the container and determines, based on the proximity signal, a distance between the container and the wearable computing device. The wearable computing device is configured to monitor its motion sensor for the first motion pattern when the distance is below a minimum distance threshold. As such, in this example, the wearable computing device selectively monitors for the first motion pattern when the wearable computing device is in range of the container, and therefore when prescription adherence is more likely.

The wearable computing device and software also include an input that allows a user to indicate that they intend to adhere to a prescription regardless of whether the wearable computing device. As such, whether the wearable computing device is selectively monitoring or not, the user can cause the wearable computing device to begin monitoring after such input is provided. The input may be provided through any suitable means including a voice command, a touchscreen input, or a predefined motion.

As described herein, the systems and methods described are configured to use a wearable computing device to define "gestures" associated with a patient following a prescription and to monitor for adherence to such prescriptions. More particularly, the systems and methods are capable of tracking adherence to prescription types such as those described above. In one example, the gestures are defined based on a patient (or user) training software of the wearable computing device to recognize the gesture patterns associated with a particular prescription. In such an example, the wearable computing device applies such training for monitoring or detection of prescription adherence. In another example, the software of the wearable computing device includes default definitions for gestures. As such, the software is able to detect gestures based on such default definitions. Further, as described above, the systems and methods are configured to provide additional functions including: (a) confirm adherence to a prescription with a user, guardian, or healthcare provider; (b) update a record of compliance with a prescription or prescriptions based on detected adherence; and (c) facilitate timely prescription refills and renewals based on detected and confirmed prescription adherence.

The wearable computing device may also be described as part of a prescription adherence system. The prescription adherence system contains the wearable computing device. In some examples, the prescription adherence system also includes other systems such as the prescription management server and third-party computing devices such as a guardian computing device, a healthcare provider computing device, and a user mobile computing device. The wearable computing device includes at least a processor, a memory, and at least one motion sensor. Where the prescription adherence includes other systems, the wearable computing device is in networked communication with some or all of such systems.

In the example embodiment, the wearable computing device is configured to execute a mobile software application ("software" or "wearable app") that provides the interfaces and methods described herein. In some embodiments, the wearable app is associated with a related application that is available on other user computing devices such as a user mobile computing device. In one example, the related application ("mobile app") is available on mobile computing devices including smartphones or tablet computing devices. As described herein, the mobile app may be used to present information that may not easily be provided on a smartwatch or other wearable computing devices, and similarly receive information that may not easily be received on a smartwatch or other wearable computing devices. As such, in these embodiments, the mobile app may be used to facilitate some of the methods described. For example, the mobile app may allow a user to configure the presentation of the user interfaces described and to facilitate user authentication for certain parts of the methods described. Further, another related application ("compliance app") may be available on other mobile computing devices including smartphones or tablet computing devices. In some examples, the compliance app receives information regarding patient (or user) adherence to prescriptions and presents such information to a healthcare provider or a guardian.

As described herein, the wearable app presents information and interfaces related to user prescriptions. The information presented may include an identifier or identifiers to identify the prescription and prescription type. The identifier or identifiers are configurable (through any suitable means including the wearable app and the mobile app) to obscure the actual text (or actual identifiers) of the prescription name or prescription type, to protect patient health data. Because the wearable app also facilitates refills and renewals, information presented may include, for example, the number of doses available for a particular prescription, the number of refills available for a particular prescription, the amount of time remaining before the user is prescribed to take a next dose of a particular prescription, an alert indicating that a next dose of a particular prescription should be taken, confirmation user interfaces to confirm that a motion pattern corresponding to a gesture pattern related to prescription adherence, and other user alerts. In some embodiments, the wearable app is further configured to present such information and interfaces for multiple pharmaceutical prescriptions. In the example embodiment, the information and interfaces for each of the multiple pharmaceutical prescriptions can be distinguished by any suitable means including using numeric indicators, pseudonyms, graphics, or color codes.

This approach protects the security of patient health information because the user interfaces described present information in obscured forms. As such, third parties without knowledge of patient configuration selections cannot determine what the indicators and terms of the user interfaces represent. As such, the configuration tools described (whether on the mobile app or through other similar means) provide an abstraction layer that protects patient health information and prevents disclosure of such information to third parties.

Further, in some examples, requests for refills or renewals on the wearable app may require secondary authentication. In such examples, a user may initially select a renewal or refill on the wearable app before being prompted to authenticate the renewal or refill request on the mobile app. As explained herein, authentication may be performed using any suitable method including, for example, a personal identification number (PIN), a password, a challenge phrase, two-factor authentication, or biometric authentication such as fingerprint or retinal scan. In other examples a user may authenticate a renewal or refill on the wearable app using similar authentication methods.

In the example embodiment, the set of prescription plan data is received, directly or indirectly, from the prescription management server. In other examples, the set of prescription plan data may be received from any suitable data source including, for example, other user computing devices such as the mobile computing device, or a server associated with a pharmacy, insurer, or healthcare provider. In one example, the wearable computing device may receive the set of prescription plan data through a "push" from an external system such as the prescription management server. In another example, the wearable computing device may initiate a "pull" request to the external system, which results in transmission of the set of prescription plan data to the wearable computing device.

The systems and methods described herein are further designed to ensure that the patient data is kept secure, private, and confidential as necessary according to any appropriate regulations or laws including the Health Insurance Portability and Accountability Act (HIPAA). As such, any data related to prescriptions stored on the wearable computing device, the prescription management server, and any other computing device is appropriately stored and transmitted using appropriate security and encryption.

As described above, in some examples, the wearable computing device is configured to synchronize with the prescription management server. In further examples, the wearable computing device may synchronize with other systems including mobile user computing devices. In the example embodiment, the wearable computing device synchronizes the inventory level. In some examples, any appropriate data may be synchronized including the set of prescription plan data and any adherence information provided by the user including, for example, user input regarding adherence and the timing of such input.

In some examples, the wearable computing device provides interfaces allowing a user to request a refill of a particular prescription or a renewal of a particular prescription. Generally, pharmaceutical prescriptions may be associated with a certain amount of refills that allow a patient to receive a certain amount of new pharmaceuticals without a new prescription. Typically, the amount of refills available for a prescription is a specified numeric amount.

Generally, the systems and methods described herein are configured to perform at least the following steps that may be performed in any order, and using any permutation of such steps: receive a set of prescription plan data defining a prescription for a pharmaceutical associated with a user of the wearable computing device; receive a gesture pattern of movement of the wearable computing device, the gesture pattern indicating that a patient is adhering to the prescription; detect, with the motion sensor, a first motion pattern associated with the wearable computing device; analyze the first motion pattern to determine if the gesture pattern has been performed; upon determining that the gesture pattern has been performed, update a prescription usage record; process the set of prescription plan data to identify a period of time in which the user is expected to adhere to the prescription; monitor the motion sensor for the first motion pattern during the identified period of time; determine that the wearable computing device is in a training mode to define the gesture pattern; detect, with the motion sensor, a training motion pattern associated with the wearable computing device; define the gesture pattern based on the training motion pattern; process the prescription usage record and the set of prescription plan data to determine an inventory level associated with the prescription; determine that the inventory level has fallen below a minimal threshold; present the user with an interface to request a refill of the prescription; upon determining that the gesture pattern has been performed, present the user with a confirmation interface to confirm adherence to the prescription; upon receiving a confirmation at the confirmation interface, update the prescription usage record; receive a proximity signal from a communication interface associated with the container; determine, based on the proximity signal, a distance between the container and the wearable computing device; and monitor the motion sensor for the first motion pattern when the distance is below a minimum distance threshold.

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104.

The system 100 may also include one or more user device(s) 108. A user, such as a pharmacist, patient, data analyst, health plan administrator, etc., may access the benefit manager device 102 or the pharmacy device 106 using the user device 108. The user device 108 may be a desktop computer, a laptop computer, a tablet, a smartphone, a wearable electronic device, etc.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long-term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. The member may order their medicine through a wearable device that has communication capability, e.g., a smart watch. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in a storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process. The result of the adjudication can be sent to the wearable device for display to the member, e.g., through a display on the wearable device.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfillment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 can also include a unique identifier for the wearable device associated with a patient. In an example, the member data 120 identifies the patient wearable device. In an example, the member data 120 identifies the caregiver's wearable device, with the caregiver being identified as caring for a patient receiving the medication. In an example, the member data 120 identifies the parent's device or guardian's wearable device, with the parent or guardian being identified as caring for a minor patient receiving the medication. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc. The message preferences can include types of indicators to be displayed on the wearable device as described herein. The message preferences can include the length, width and color of the indicators to be displayed on the wearable device. In an example embodiment, the default indicators are color coded to match the color of the individual drugs, e.g., pills, tablets, capsules and the like, being filled at the pharmacy 106. The member data 120 can also include a gesture profile, which may be based on the member's actual motions as determined by a wearable device or based on a motion model. The motion model can be stored in a server and include attributes related to the characteristics of the member (age, sex, handedness, height, and the like). The motion model can be used to derive a gesture profile for an individual member and download it to their wearable device.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably. In some instances the patient may be a user who is a dependent of the member.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in a solid form, e.g., pill form, tablet form, capsule form or the like), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include usernames, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.). The prescription data 126 can also include the type of container that the prescription is dispensed to the member, which can be used to select or determine the type of gesture that a member would use to dispense their medication. For example, a member may request childproof caps. This will require a downward press of the cap while rotating the cap whereas a non-childproof cap would not require pressing down while rotating.

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
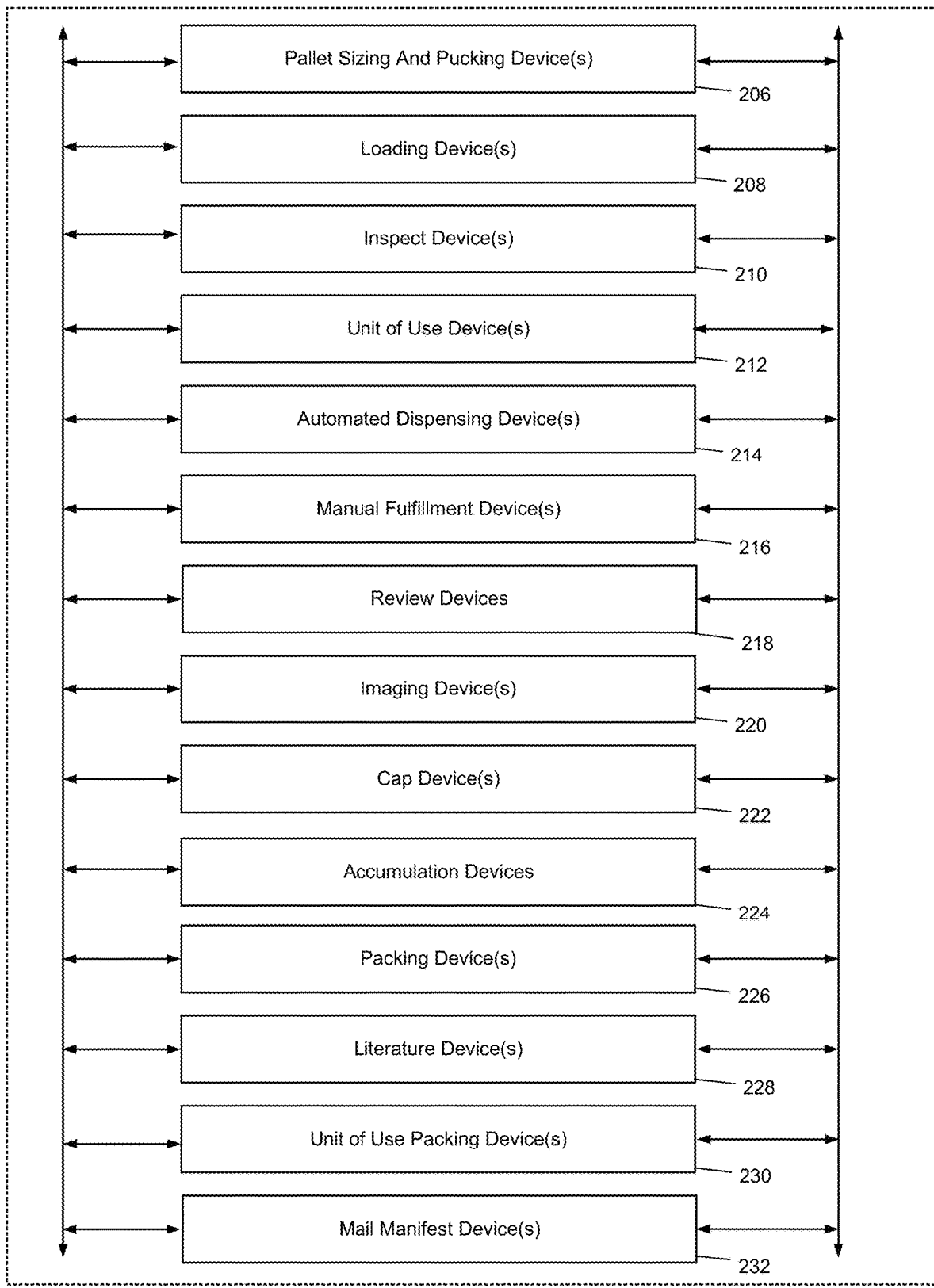
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device (s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists. A unit of use packaging may require different member movements to retrieve their medication relative to a bottle type container that is moved in the pallets. The system can track the packaging type and report it to the system to select a motion profile for the member relative to a specific drug.

While the pharmacy fulfillment device 112 in FIG. 2 is shown to include single devices 206-232, multiple devices may be used. When multiple devices are present, the multiple devices may be of the same device type or models or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
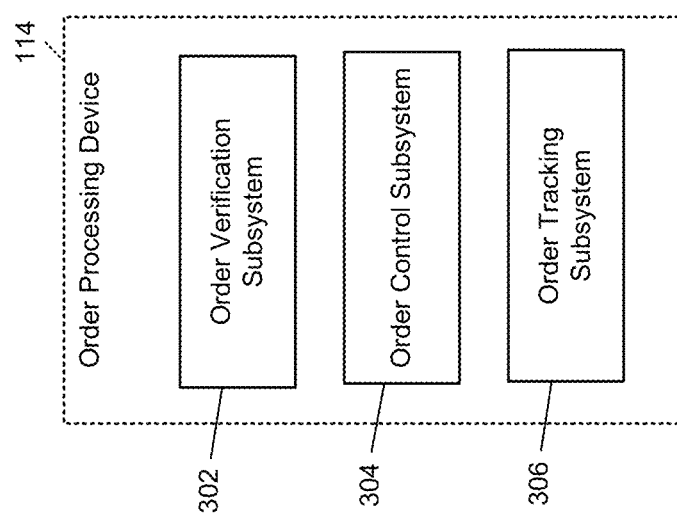
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may include order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Figure 4:
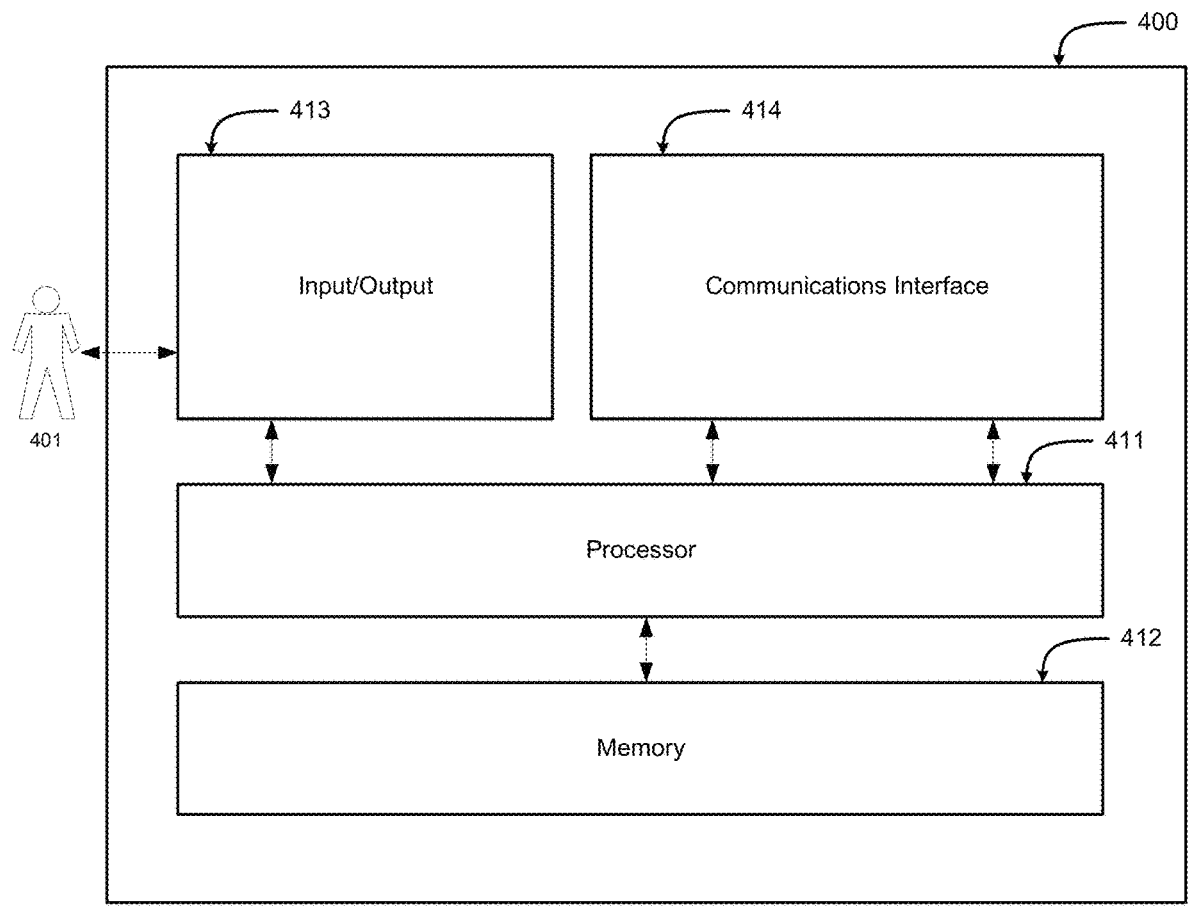
FIG. 4 is a functional block diagram of an example computing device that may be used in the environments described herein.
Figure 5:
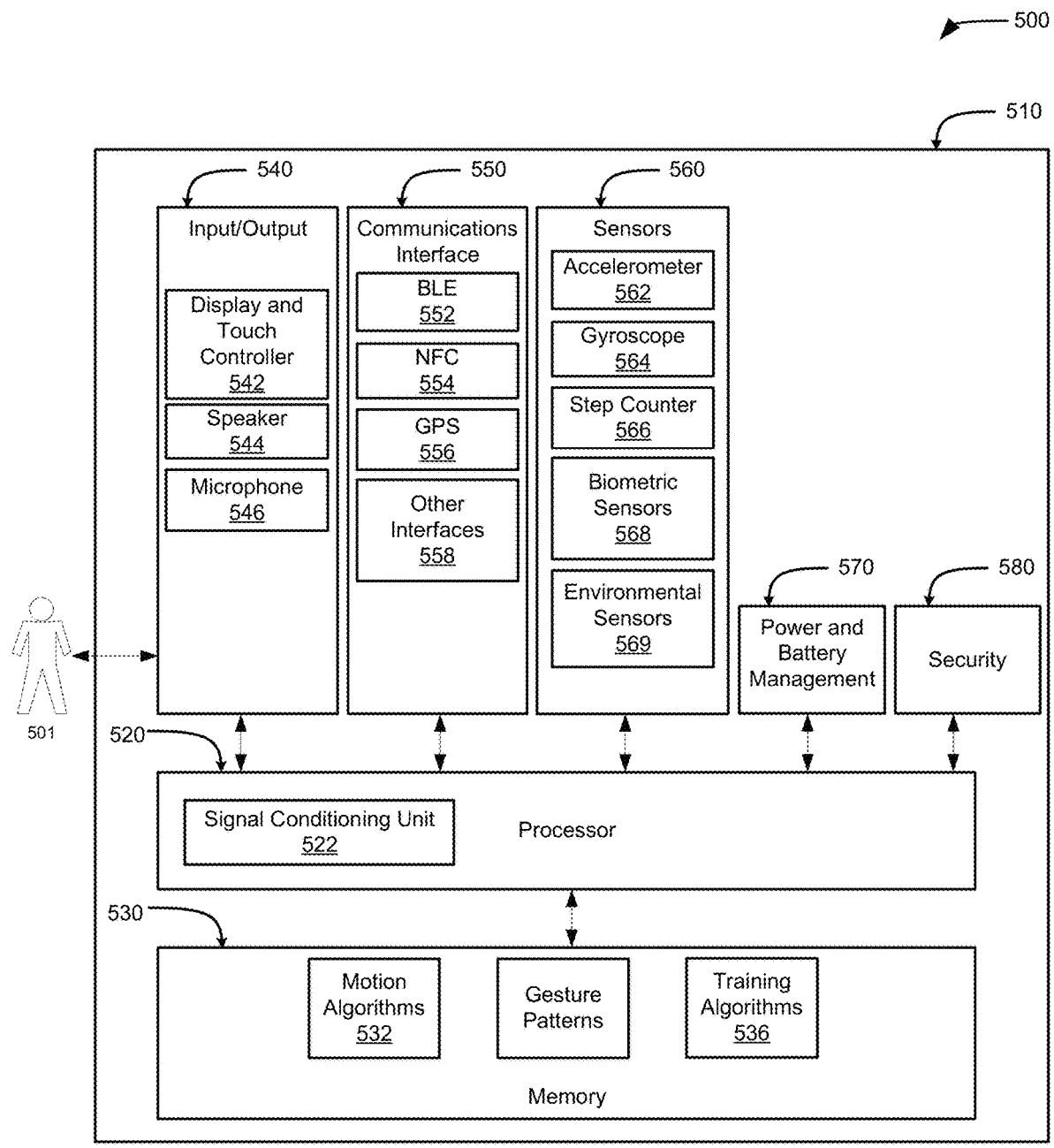
FIG. 5 is a functional block diagram of an example wearable computing device that may be used in the environments described herein.

FIG. 4 is a functional block diagram of an example computing device 400 that may be used in the environments described herein. Specifically, computing device 400 illustrates an exemplary configuration of a computing device. Computing device 400 illustrates an exemplary configuration of a computing device operated by a user 401 in accordance with one embodiment of the present invention. Computing device 400 may include, but is not limited to, a mobile computing device, a user computing device, a prescription management server, a host device, an inventory device, and any other system described herein. Computing device 400 may also describe a wearable computing device, however a more detailed exemplary wearable computing device is shown in FIG. 5. Computing device 400 may also include pharmacy devices 106 including pharmacy fulfillment devices 112, order processing devices 114, and pharmacy management devices 116, storage devices 110, benefit manager devices 102, and user devices 108 (all shown in FIG. 1), mobile computing devices, stationary computing devices, computing peripheral devices, smart phones, wearable computing devices, medical computing devices, and vehicular computing devices. Alternatively, computing device 400 may be any computing device capable of monitoring and facilitating prescription adherence by a patient, as described herein. In some variations, the characteristics of the described components may be more or less advanced, primitive, or non-functional.

In the exemplary embodiment, computing device 400 includes a processor 411 for executing instructions. In some embodiments, executable instructions are stored in a memory area 412. Processor 411 may include one or more processing units, for example, a multi-core configuration. Memory area 412 is any device allowing information such as executable instructions and/or written works to be stored and retrieved. Memory area 412 may include one or more computer readable media.

Computing device 400 also includes at least one input/output component 413 for receiving information from and providing information to user 401. In some examples, input/output component 413 may be of limited functionality or non-functional as in the case of some wearable computing devices. In other examples, input/output component 413 is any component capable of conveying information to or receiving information from user 401. In some embodiments, input/output component 413 includes an output adapter such as a video adapter and/or an audio adapter. Input/output component 413 may alternatively include an output device such as a display device, a liquid crystal display (LCD), organic light emitting diode (OLED) display, or "electronic ink" display, or an audio output device, a speaker or headphones. Input/output component 413 may also include any devices, modules, or structures for receiving input from user 401. Input/output component 413 may therefore include, for example, a keyboard, a pointing device, a mouse, a stylus, a touch sensitive panel, a touch pad, a touch screen, a gyroscope, an accelerometer, a position detector, or an audio input device. A single component such as a touch screen may function as both an output and input device of input/output component 413. Input/output component 413 may further include multiple sub-components for carrying out input and output functions.

Computing device 400 may also include a communications interface 414, which may be communicatively coupleable to a remote device such as a remote computing device, a remote server, or any other suitable system. Communication interface 414 may include, for example, a wired or wireless network adapter or a wireless data transceiver for use with a mobile phone network, Global System for Mobile communications (GSM), 3G, 4G, LTE, 5G or other mobile data network or Worldwide Interoperability for Microwave Access (WIMAX). Communications interface 414 is configured to allow computing device 400 to interface with any other computing device or network using an appropriate wireless or wired communications protocol such as, without limitation, BLUETOOTH®, Ethernet, or IEE 802.11. Communications interface 414 allows computing device 400 to communicate with any other computing devices with which it is in communication or connection.

FIG. 5 is a functional block diagram 500 of an example wearable computing device 510 that may be used in the environments described herein. Wearable computing device 510 reflects a more specific, more detailed version of computing device 400 (shown in FIG. 4) and accordingly includes similar structures with additional elements. In the example embodiment, wearable computing device 510 is used by user 501 and coupled to a part of the body of user 501 or worn by user 501. In a typical example, wearable computing device 510 is worn at the wrist or arm of user 501. Wearable computing device 510 includes a processor 520 that is similar to processor 411 of FIG. 4, a memory 530 that is similar to memory 412 of FIG. 4, an input/output that is similar to input/output 413 of FIG. 4, and a communications interface 540 that is similar to communications interface 414 of FIG. 4. Further, in the example embodiment, processor 520 includes a signal conditioning unit 522 that is used to process the signals provided by the components of the wearable computing device 510 including components 542, 544, 546, 562, 564, 566, 568, and 569. More particularly, and relevant to the disclosure herein, signal conditioning unit 522 is used to process any signals provided by sensors 560 and sensor components 562, 564, 566, 568, and 569 to determine values and attributes related to motion detected by such sensors and sensor components. In some examples, memory 530 also includes software encoded thereon to effect the methods described herein. Specifically, memory 530 includes motion algorithms 532 that, upon processing by processor 520, process sensor data related to motions received by sensors 560 and sensor components 562, 564, and 566 and any other pertinent sensors to determine the quantitative and qualitative characteristics of motion and motion patterns including distances traveled, locations of the wearable computing device 510 over time, changes in orientation of the wearable computing device 510 over time, acceleration of the wearable computing device 510 over time, and generally the motion of the wearable computing device 510 over time. Memory 530 also includes gesture patterns 534 that describe gesture patterns (whether trained or pre-defined) and associated quantitative and qualitative characteristics of motion and motion patterns including distances traveled, locations of the wearable computing device 510 over time, changes in orientation of the wearable computing device 510 over time, acceleration of the wearable computing device 510 over time, and generally the motion of the wearable computing device 510 over time. Memory 530 also includes training algorithms 536 which, when executed, effect the training functions of the software (or wearable app). Specifically, when executed, training algorithms 536 guide user 501 through training by providing prompts (through the touchscreen interface or audio commands) to carry out the steps associated with adherence to a particular prescription, based in part on the set of prescription plan data associated with the user.

Wearable computing device 510 also includes an input/output 540 with input/output components 542, 544, and 546. Display and touch controller 542 includes a display screen that can receive haptic inputs and present images and video using any suitable display including a liquid crystal display (LCD), organic light emitting diode (OLED) display, or "electronic ink" display. Speaker 544 is configured to provide audio output to a user and microphone 546 is configured to receive audio input including input from a user. Input/output 540 is also configured to receive other related inputs including keyboard inputs (where a keyboard is included) and haptic inputs as well as receive tactile inputs and provide tactile outputs such as vibrations.

Communications interface 550 includes a plurality of interfaces for communications to other devices including communications components 552, 554, 556, and 558 and accordingly provide communications using suitable protocols including cellular communications, Bluetooth® connectivity, near field communication (NFC), global positioning system (GPS), global system for mobile communications (GSM), universal mobile telecommunications service (UTMS), WiFi, and Zigbee. Communications component 552 provides communication capabilities using Bluetooth® interface 552, nearfield communication interface 554, GPS interface 556, and other interfaces 558. Other interfaces provide communication using known communications standards including but not limited to WiFi, Zigbee, GSM, and UMTS.

Sensors 560 are configured to detect conditions related to user 501 and environmental conditions. Pertinent to the systems and methods described herein, sensors 560 include motion sensors 562, 564, and 566 that detect location, changes in location (or motion) over time, orientation, and changes in orientation over time. Specifically, accelerometer 562 is used to measure acceleration forces acting on the wearable computing device 510 including static forces (e.g., gravity) and dynamic forces (e.g., motion of the accelerometer 562 and wearable computing device 510 caused by user 501 or external conditions). Accelerometer 562 is configured to detect acceleration and determine signals that can be used to determine absolute motion, relative motion, absolute location, and relative location of wearable computing device 510. Sensors 560 also includes a gyroscope 564 used to determine the orientation and location of wearable computing device 510. In the example embodiment, gyroscope 564 is a three-axis gyroscope. Sensors 560 also includes step counter 566 used to detect vibrations and determine whether a user has made a step with the feet of the user. Sensors 560 also include biometric sensors 568 used to take measurements from a user 501 using suitable means (e.g., light measurements) to determine biometrics including pulse rate pulse or heart rate, hydration level, oxygen level, and glucose levels. Sensors 560 also include environmental sensors 569 that may take measurements of the environmental conditions (e.g., temperature, pressure, and humidity). As described above, in some examples the measurements of sensors 560 are processed by signal conditioning unit 522 before converting the measured readings into data.

Wearable computing device 510 also includes power and battery management services 570. Power and battery management services 570 are used to manage the power usage and charging of wearable computing device 510 including battery charger services, wireless battery charger services, power management units, and other necessary components. Wearable computing device 510 also includes security services 580 that provide necessary components for securing information transmitted to or from wearable computing device 510 and secure information stored by wearable computing device 510 on, for example, memory 530.

Figure 6:
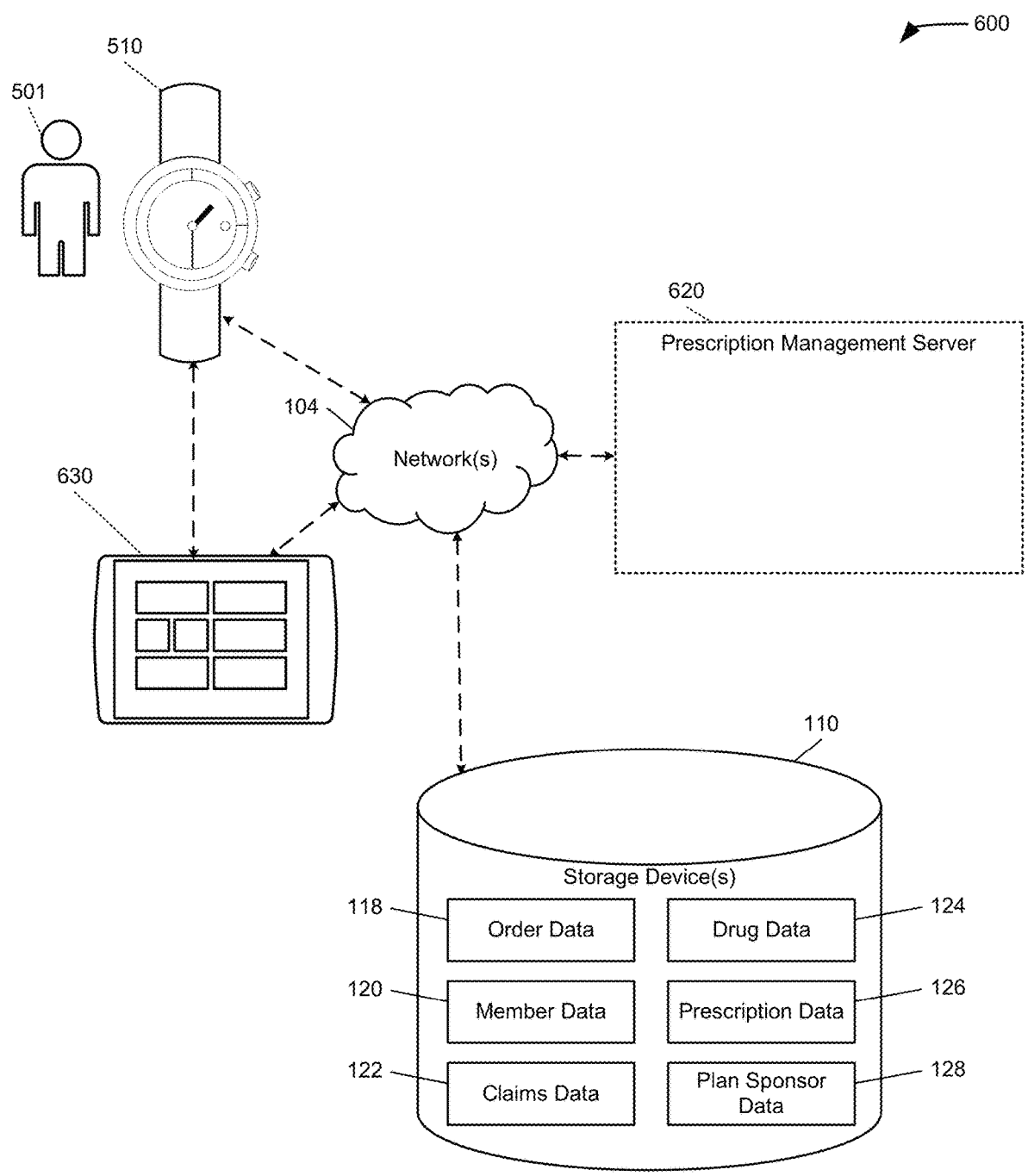
FIG. 6 is a functional block diagram of a prescription adherence system for identifying gestures of prescription adherence performed by a patient, including a wearable computing device and a prescription management server and other computing devices shown in FIGS. 4 and 5.

FIG. 6 is a functional block diagram of a prescription adherence system 600 for identifying gestures of prescription adherence performed by a patient 501, including a wearable computing device 510 and a prescription management server 620 and other computing devices. Specifically, prescription adherence system 600 includes wearable computing device 510, prescription management server 620, and mobile computing device(s) 630. Devices 510, 620, and 630 are in networked communication via network 104. Devices 510, 620, and 630 also have access to pertinent information related to prescription plan data, adherence data, refill data and refill orders, renewal data and renewal orders, prescription information, user shipping information, and user billing information. Such information may be stored in any of devices 510, 620, and 630 and may be stored at, and obtained from, storage device(s) 110.

Figure 7:
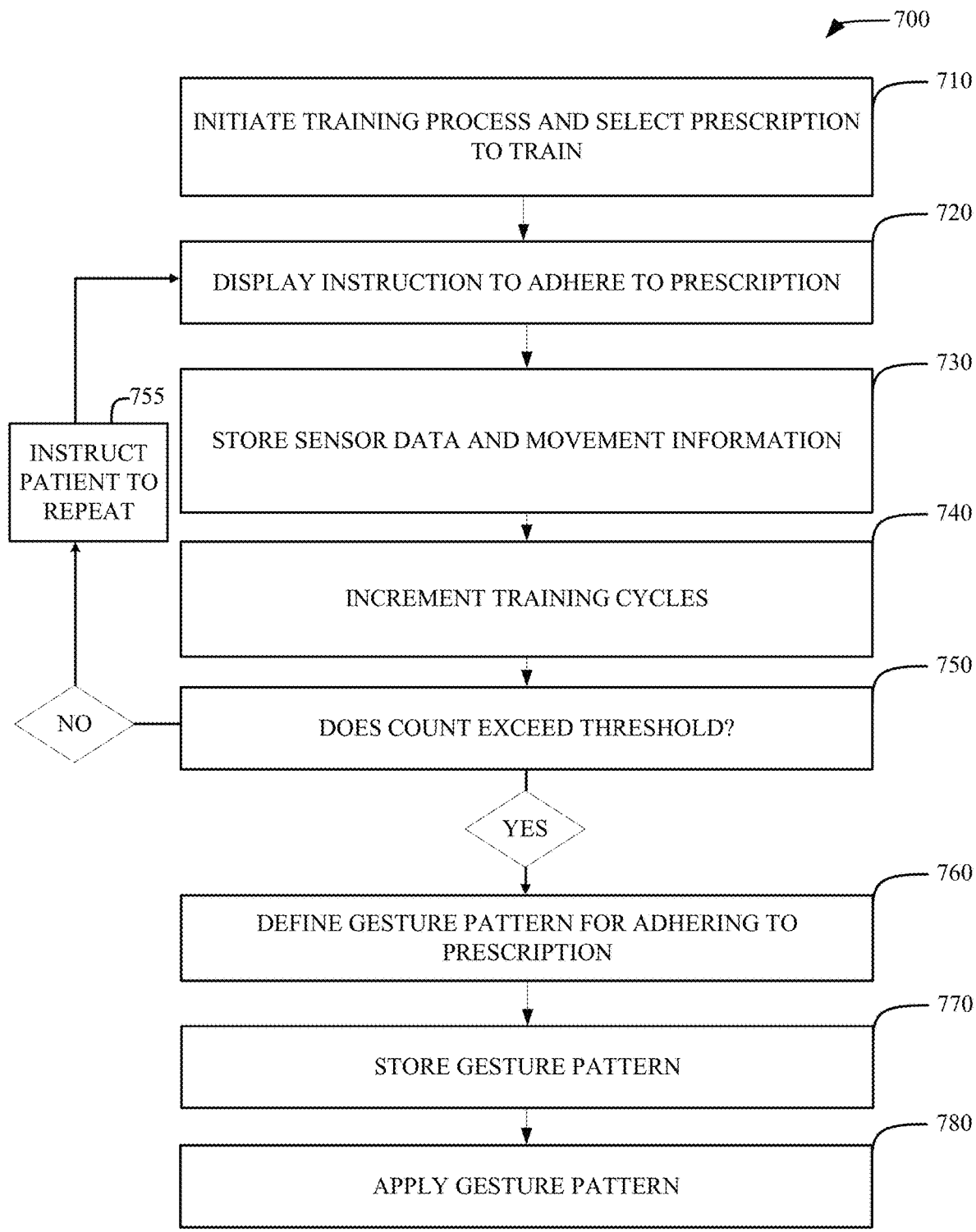
FIG. 7 is a flow diagram representing a method for training the prescription adherence system of FIG. 6 to identify gestures of prescription adherence performed by a patient.

FIG. 7 is a flow diagram 700 representing a method for training the prescription adherence system 600 (shown in FIG. 6) to identify gestures of prescription adherence performed by a patient. Specifically, diagram 700 reflects the process performed by a wearable computing device 510 when user 501 "trains" the software (or wearable app) to learn a gesture pattern associated with adherence to a particular prescription prescribed to patient 501. Initially, wearable computing device 510 provides an interface that allows user 501 to initiate 710 a training process. If user 501 is associated with multiple prescriptions (as defined in prescription plan data), wearable computing device 510 also provides an interface to allow user 501 to select a prescription to train. User 501 may also be prompted by wearable computing device 510 to confirm the prescription being trained.

Wearable computing device 510 also displays 720 instructions to adhere to a particular prescription, based on the steps defined for that prescription in the prescription plan data. Exemplary steps are outlined above in detail. Wearable computing device 510 displays 720 each step in the sequence until user 501 adheres to each step. When user 501 performs each step, wearable computing device 510 stores 730 sensor data and movement information captured by wearable computing device 510 during the step. When a complete training cycle (i.e., a cycle including all steps for adhering to a particular prescription) has been completed, wearable computing device 510 increments 740 the number of completed training cycles. (The initial number of training cycles is set to zero by default.) Wearable computing device 510 compares the number of completed training cycles to a threshold minimum associated with the prescription and determines 750 whether the count of completed training cycles exceeds a threshold minimum. If the threshold is not exceeded, wearable computing device 510 instructs 755 user (or patient) 501 to repeat the process and returns to step 720. If the threshold is exceeded, wearable computing device 510 defines 760 a gesture pattern for adhering to a prescription and stores 770 the gesture pattern. Once the gesture pattern is so defined 760 and stored 770, wearable computing device 510 may apply 780 gesture pattern to detect whether a first motion pattern corresponds to the gesture pattern. (Where the gesture patterns are predefined, the steps of diagram 700 are performed beforehand by prior users, or simulated users.)

Figure 8:
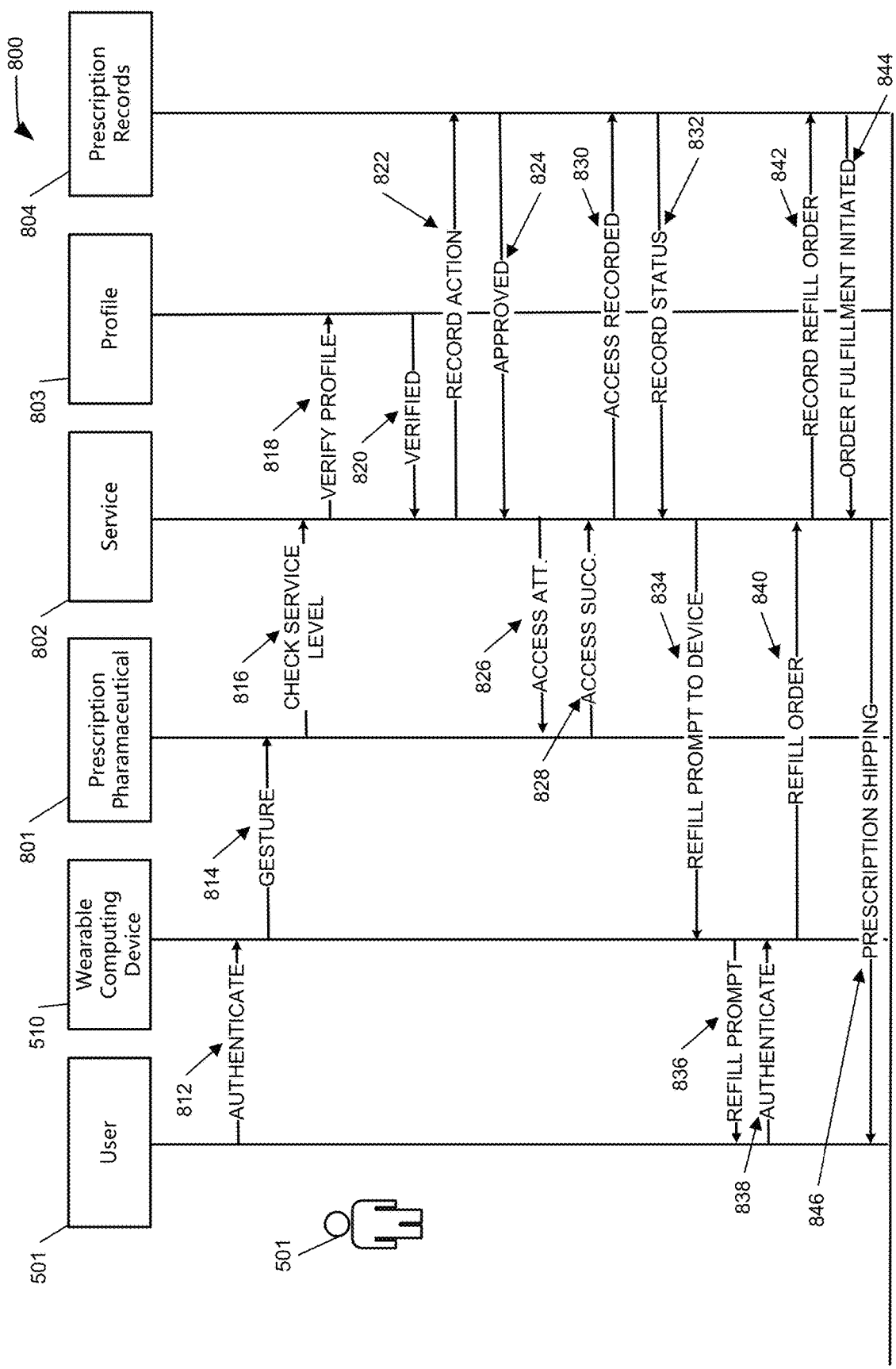
FIG. 8 is a flow diagram representing an exemplary process performed by the prescription adherence system of FIG. 6 to identify gestures of prescription adherence performed by a patient.

FIG. 8 is a flow diagram 800 representing an exemplary process performed by the prescription adherence system 600 (shown in FIG. 6) to identify gestures of prescription adherence performed by a patient 501. Diagram 800 includes indications to show entities, systems, objects, or data structures involved in each step of diagram 800. Specifically, such entities, systems, objects, and data structures include user 501, wearable computing device 510, prescription pharmaceutical 801, service 802, profile 803, and prescription records 804. In diagram 800, user 501 authenticates 812 at wearable computing device 510 by performing any necessary authentication step to confirm that user 501 is the person associated with the software (or wearable app) and associated sets of prescription plan data. As described herein, wearable computing device 510 uses software (or the wearable app) to monitor for a first motion pattern and detect a gesture. Accordingly, wearable computing device 510 detects gesture 814 performed by user 501. Wearable computing device 510 also accesses service 802 and checks 816 service level which verifies 818 the profile with a profile 803. When the profile is verified 820, service 802 records 822 the adherence action with prescription records 804

(stored locally or in another system such as prescription management server 620) and receives an approval indication 824 from prescription management server 620. User 501 attempts 826 to access prescription pharmaceutical 801 and, if successful, the attempt is recorded 828 as successful with service 802 and recorded 830 as successful with prescription records 804 which transmits 832 a status record to service 802. As noted above, wearable computing device 510 also tracks the inventory level associated with prescription pharmaceutical 510. If the inventory level falls below a minimum threshold (as described above), the wearable computing device 510 provides a refill prompt 834 to wearable computing device 510 which is presented 836 to user 501. User 501 may request a refill at wearable computing device 510 after which user 501 is prompted to authenticate 838 the request (at wearable computing device 510 in diagram 800 or on an alternative computing device such as a mobile computing device via a mobile app). Upon such verification, wearable computing device 510 transmits a refill order 840 to service 802 which records refill order 842 at with prescription record 804 at, for example, prescription management server 620. The refill order is processed, and a record is sent from, for example, prescription management server 620 to service 802 indicating the order fulfillment is initiated 844. Service 802 transmits an indication to wearable computing device 510 and user 501 indicating the prescription refill is being shipped. In parallel, the refill prescription is shipped to user 501.

Figure 9:
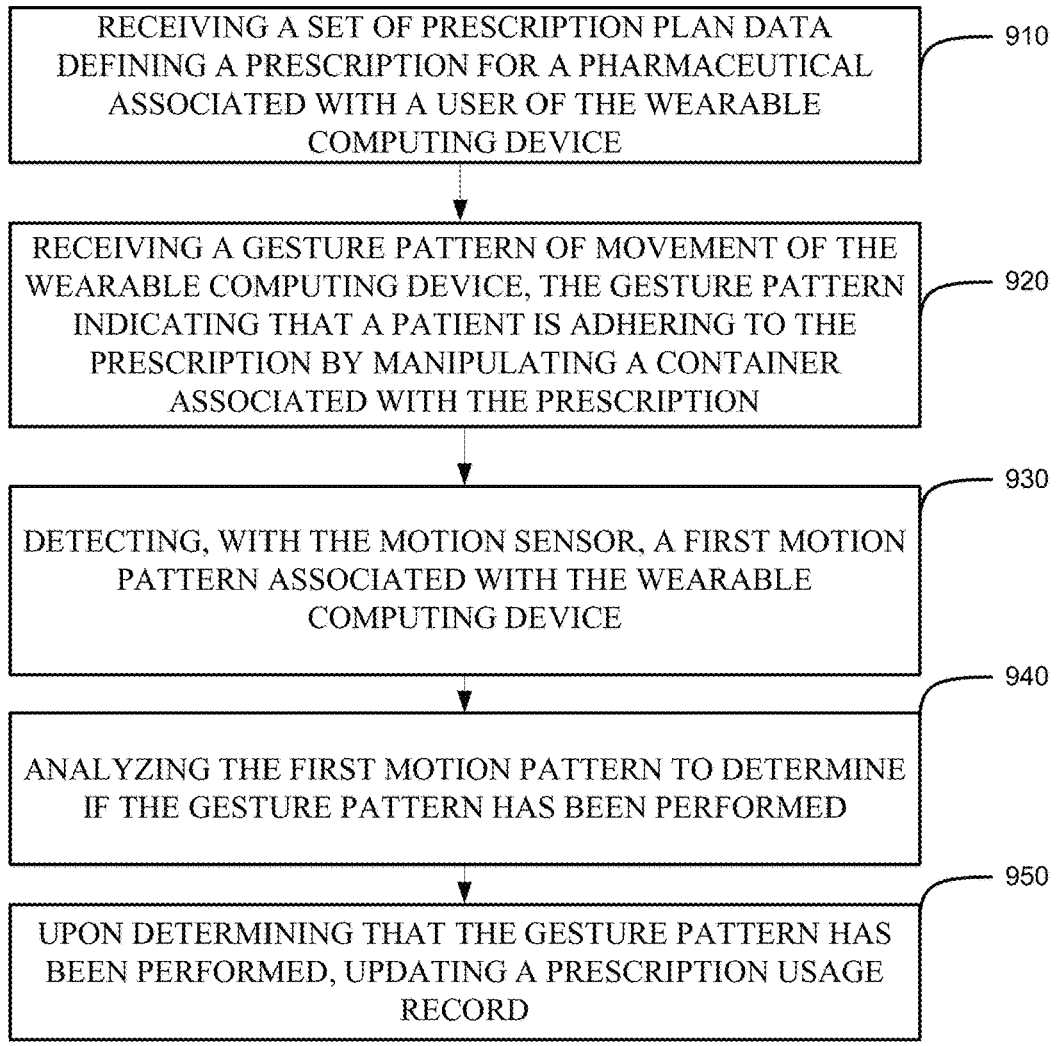
FIG. 9 is a flow diagram representing an exemplary method for identifying gestures of prescription adherence performed by the prescription adherence system shown in FIG. 6.

FIG. 9 is a flow diagram 900 representing an exemplary method for identifying gestures of prescription adherence performed by the prescription adherence system 600 (shown in FIG. 6) and specifically by wearable computing device 510 (shown in FIGS. 5 and 6). Specifically, wearable computing device 510 is configured to receive 910 a set of prescription plan data defining a prescription for a pharmaceutical associated with a user of the wearable computing device. Wearable computing device 510 is also configured to receive 920 a gesture pattern of movement of the wearable computing device. The gesture pattern indicates that a patient is adhering to the prescription. Wearable computing device 510 is further configured to detect 930, with the motion sensor, a first motion pattern associated with the wearable computing device. Wearable computing device 510 is also configured to analyze 940 the first motion pattern to determine if the gesture pattern has been performed. Upon determining that the gesture pattern has been performed, wearable computing device 510 is also configured to update 950 a prescription usage record.

Figure 10:
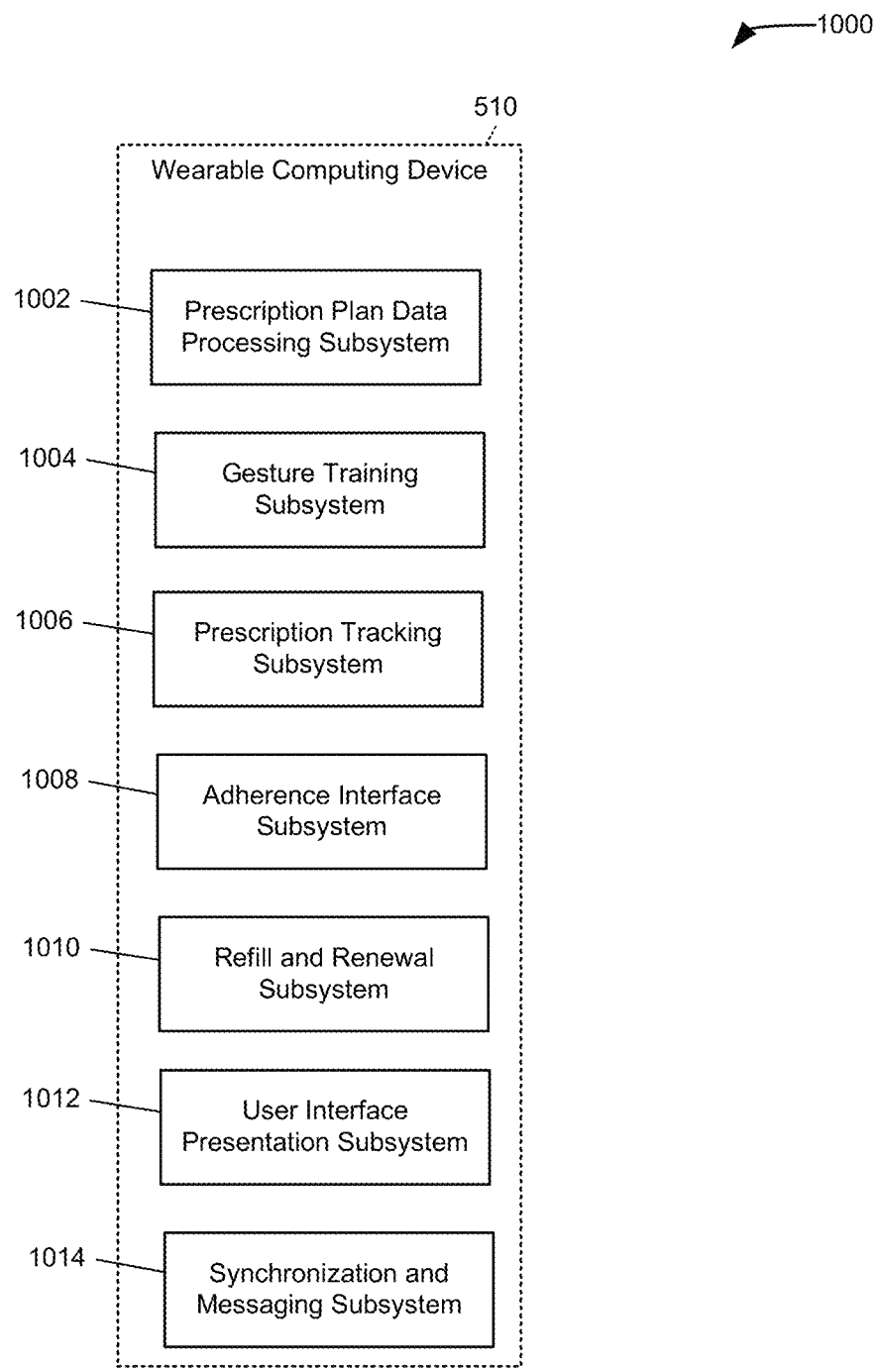
FIG. 10 is a diagram of elements of one or more example computing devices that may be used in the system shown in FIGS. 1-6.

FIG. 10 is a diagram 1000 of elements 1002, 1004, 1006, 1008, 1010, 1012, and 1014 of one or more example computing devices that may be used in the system shown in FIGS. 1-6. Specifically, elements 1002, 1004, 1006, 1008, 1010, 1012, and 1014 are used by the systems of prescription adherence system 600 (shown in FIG. 6) and specifically by wearable computing device 510 (shown in FIG. 5). Wearable computing device 510 includes a prescription plan data processing subsystem 1002 configured to process prescription plan data (or a set of prescription plan data) to identify pertinent characteristics of prescriptions to perform the methods described herein, to authenticate users as corresponding with the prescription plan, and to maintain and update prescription plan data. Wearable computing device 510 also includes a gesture training subsystem 1004 configured to facilitate the training processes on motion patterns associated with prescription adherence, as described above. Wearable computing device 510 also includes a prescription tracking subsystem 1006 configured to manage the inventory level of prescription(s) and the availability of refills and renewals for such prescription(s). Wearable computing device 510 also includes an adherence interface subsystem 1008 configured to define, configure, and present the adherence interfaces described herein. Wearable computing device 510 also includes a refill and renewal subsystem 1010 configured to manage the processes of facilitating, authenticating, and effecting refills and renewals of prescriptions. Wearable computing device 510 also includes a user interface presentation subsystem 1012 configured to define, configure, and present the user interfaces described herein. Wearable computing device 510 also includes a synchronization and messaging subsystem 1012 configured to facilitate data synchronization and messaging within prescription management system 600 and between prescription management system 600 and related systems such as a guardian computing device, a healthcare provider computing device, and a user mobile computing device.

FIGS. 11-17 depict exemplary gestures that may be detected by the wearable computing device 510 (shown in FIG. 5) in the context of the prescription adherence system 600 (shown in FIG. 6). The illustrations of FIGS. 11-17 demonstrate exemplary motions made by users (such as user 501) in the context of adherence to prescriptions, and thereby demonstrate motion patterns that may be used to define gesture patterns. Specifically, FIGS. 11-17 describe motions made by a user 501 wearing a mobile computing device 510 and accessing prescriptions to administer to the user (or patient). In FIGS. 11-17, for simplicity, three types of exemplary prescriptions are shown: (a) oral ingestion of a solid pharmaceutical in the form of a pill contained within a pill bottle; (b) intravenous injection using a syringe intramuscularly or intravenously; and (c) breathing the pharmaceutical in through the lungs after administration via an inhaler.

Figure 11:
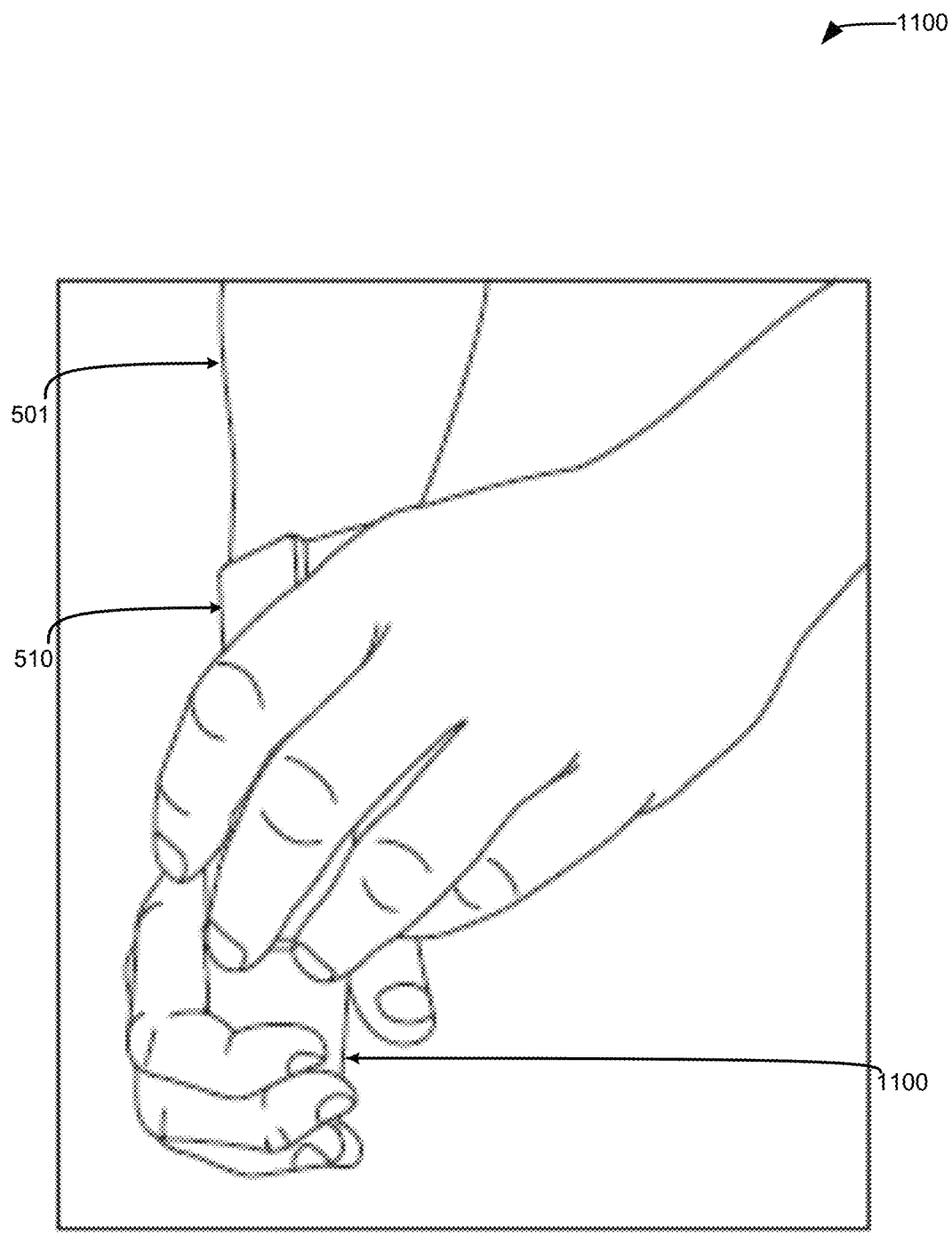
FIGS. 11-17 depict exemplary gestures that may be detected by the wearable computing device in the context of the prescription adherence system of FIG. 6.
Figure 12:
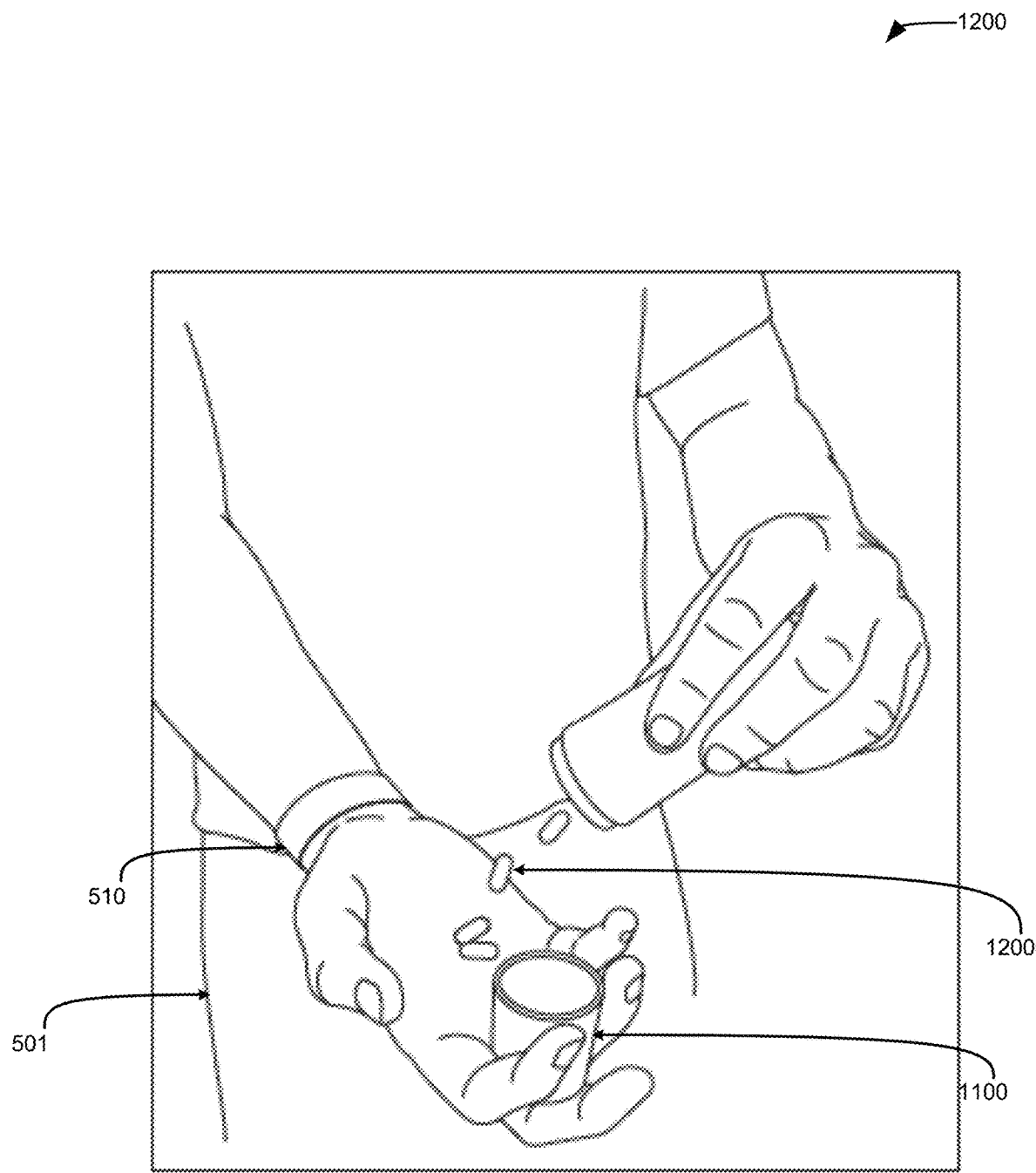

Referring to FIGS. 11-12, the illustrations depict a user 501 wearing a wearable computing device 510 seeking to access prescription pharmaceuticals 1200 contained within prescription container 1100. As shown in FIG. 11, user 501 holds prescription container 1100 and attempts to open it by rotating the cap of the container. When so doing, the hand wearing wearable computing device 510 is moved as the user opens the container and positioned in front of the body of user 501. In FIG. 12, user 501 is depicted rotating a hand wearing wearable computing device 510 to an upward position to catch the prescription pharmaceuticals 1200 dispensed from prescription container 1100. Wearable computing device 510 accordingly is configured to capture such motions of prescription adherence to define them as part of the gesture pattern. (Although not shown, wearable computing device 510 also records the positioning of the hand holding prescription pharmaceuticals 1200 upward to the mouth of the user before and upon ingestion.)

Figure 13:
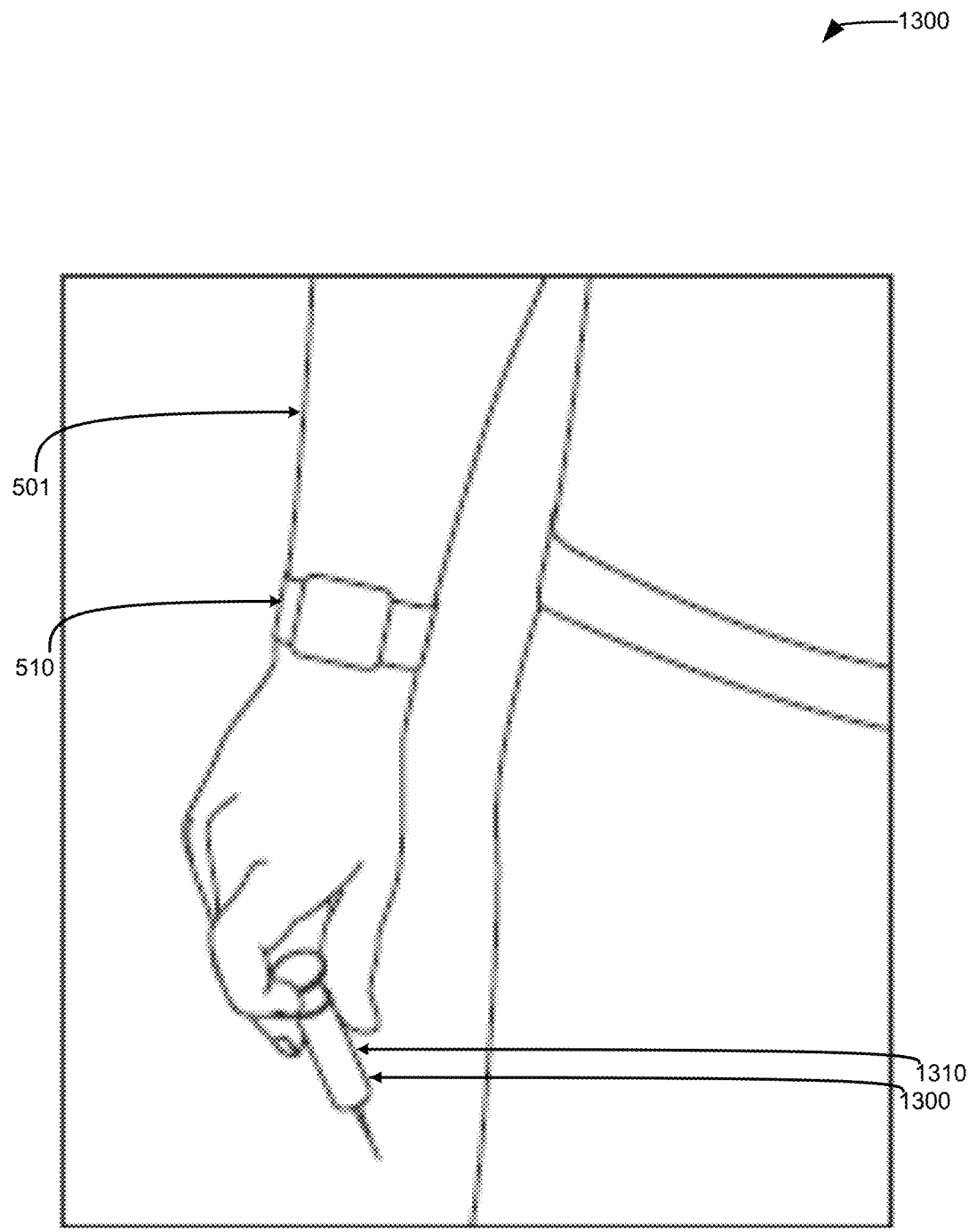
Figure 14:
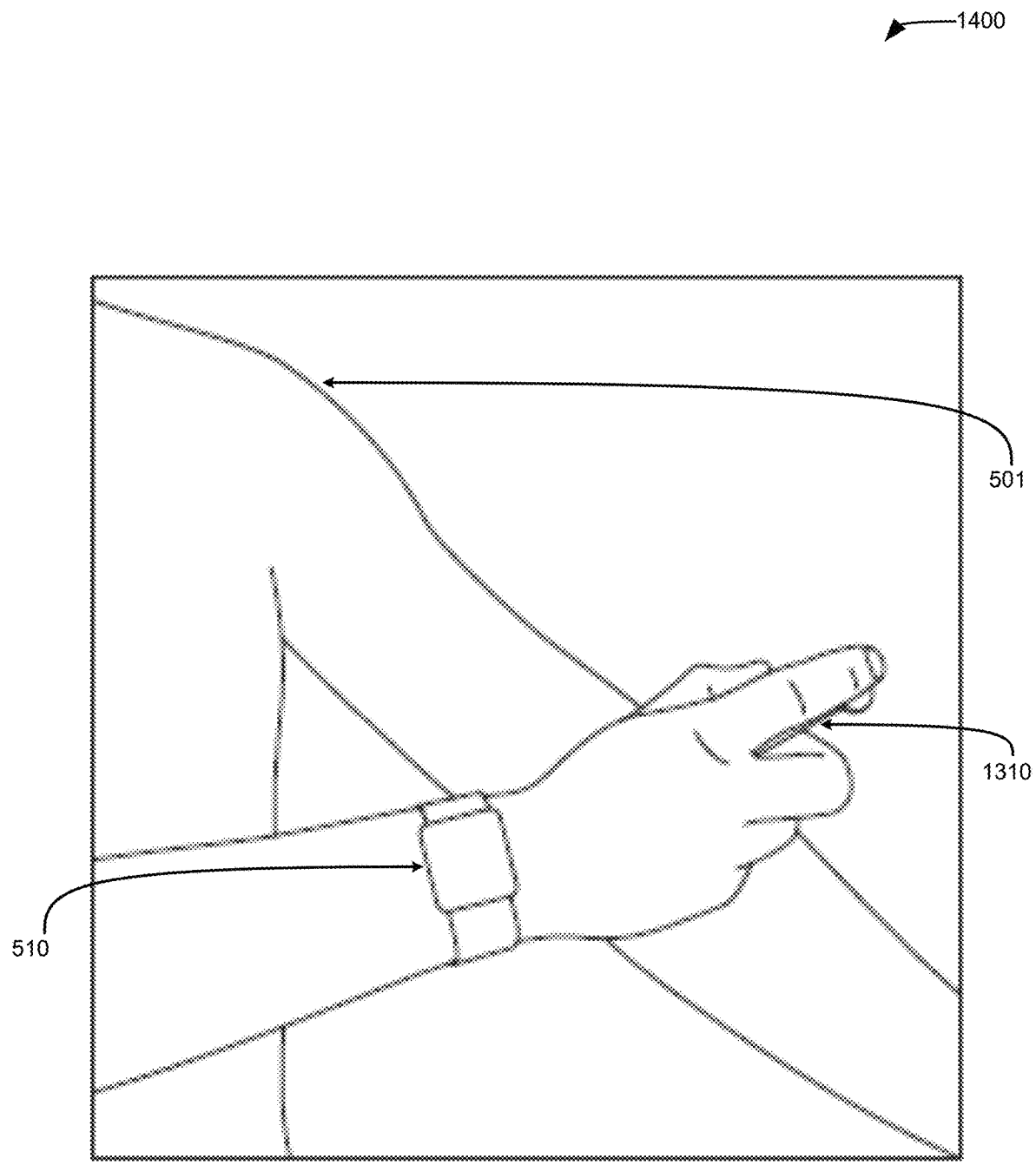
Figure 15:
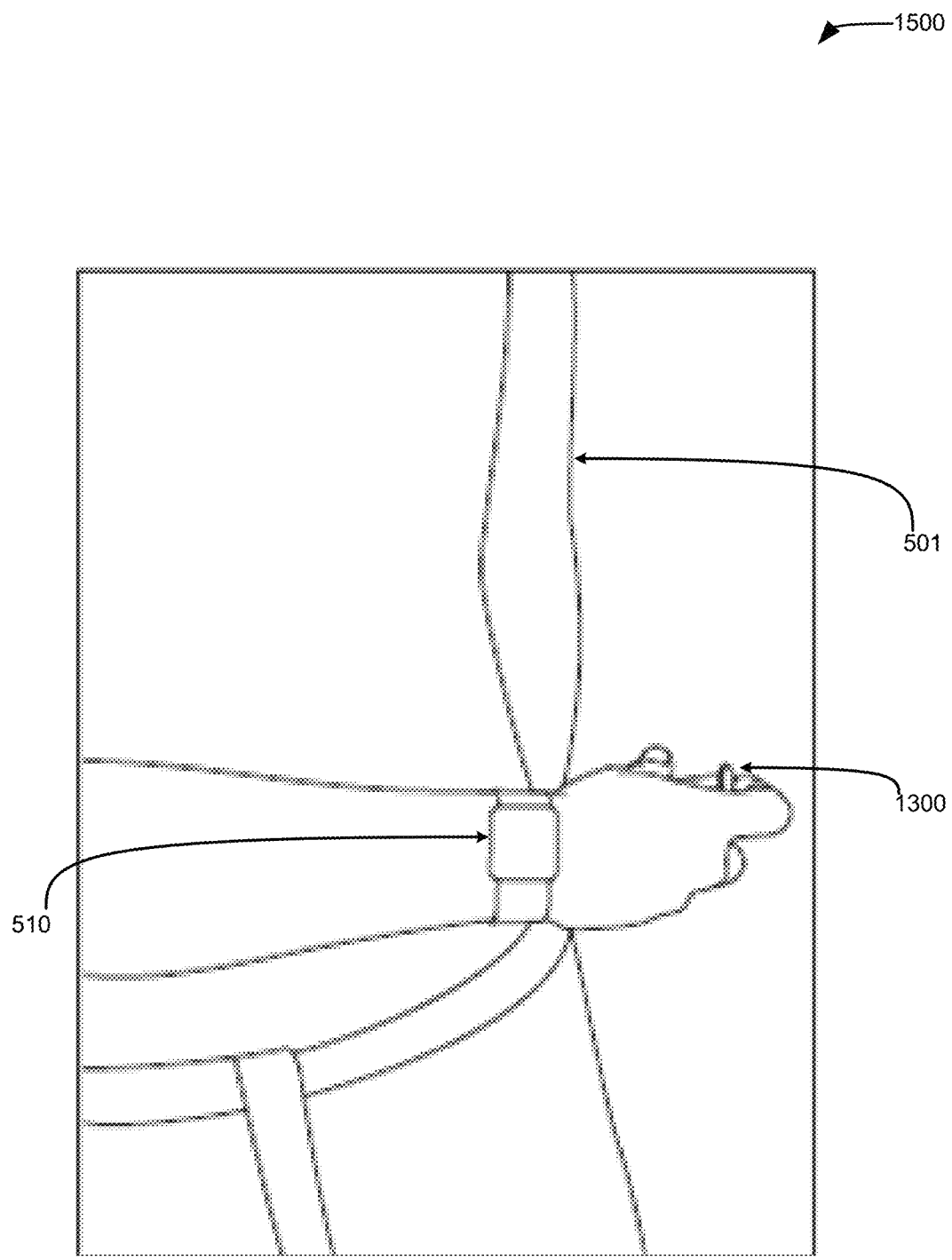

Referring to FIGS. 13-15, the illustrations depict a user 501 wearing a wearable computing device 510 seeking to inject a syringe 1300 containing a prescription pharmaceutical 1310 intravenously or intramuscularly. In FIGS. 14 and 15, user 501 moves the hand holding syringe 1300 and wearing wearable computing device 510 to a target injection site for intravenous injection (shown in FIG. 14) or intramuscular injection (shown in FIG. 15). (In FIGS. 14 and 15, prescription pharmaceutical 1310 are not visible.) Wearable computing device 510 is configured to detect the motion of the hand of user 501 when it moves syringe 1300 from a resting position (in FIG. 13) to an injection position (in FIGS. 14 and 15) and when the user moves the syringe 1300 to inject the prescription pharmaceutical 1310.

Figure 16:
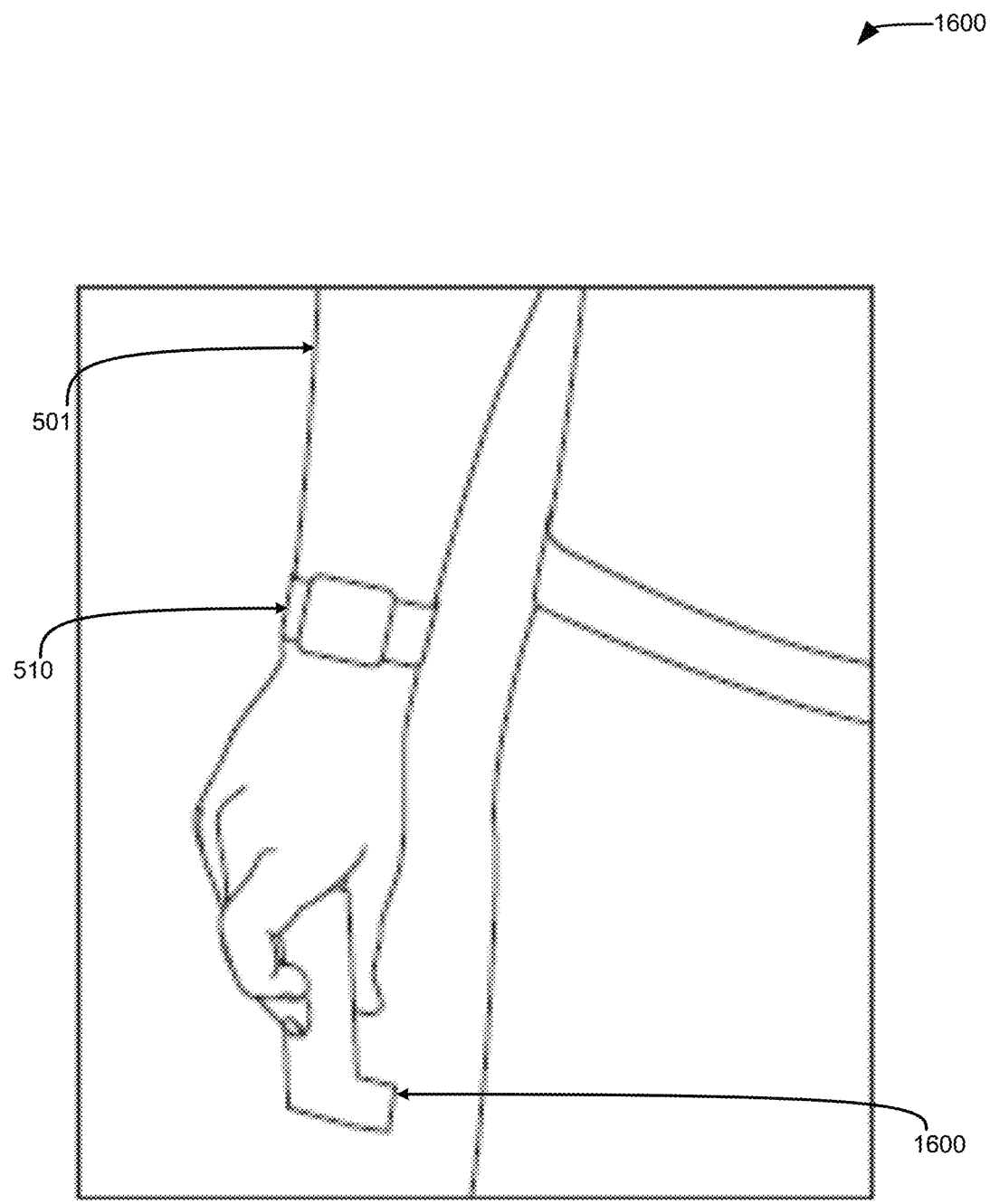
Figure 17:
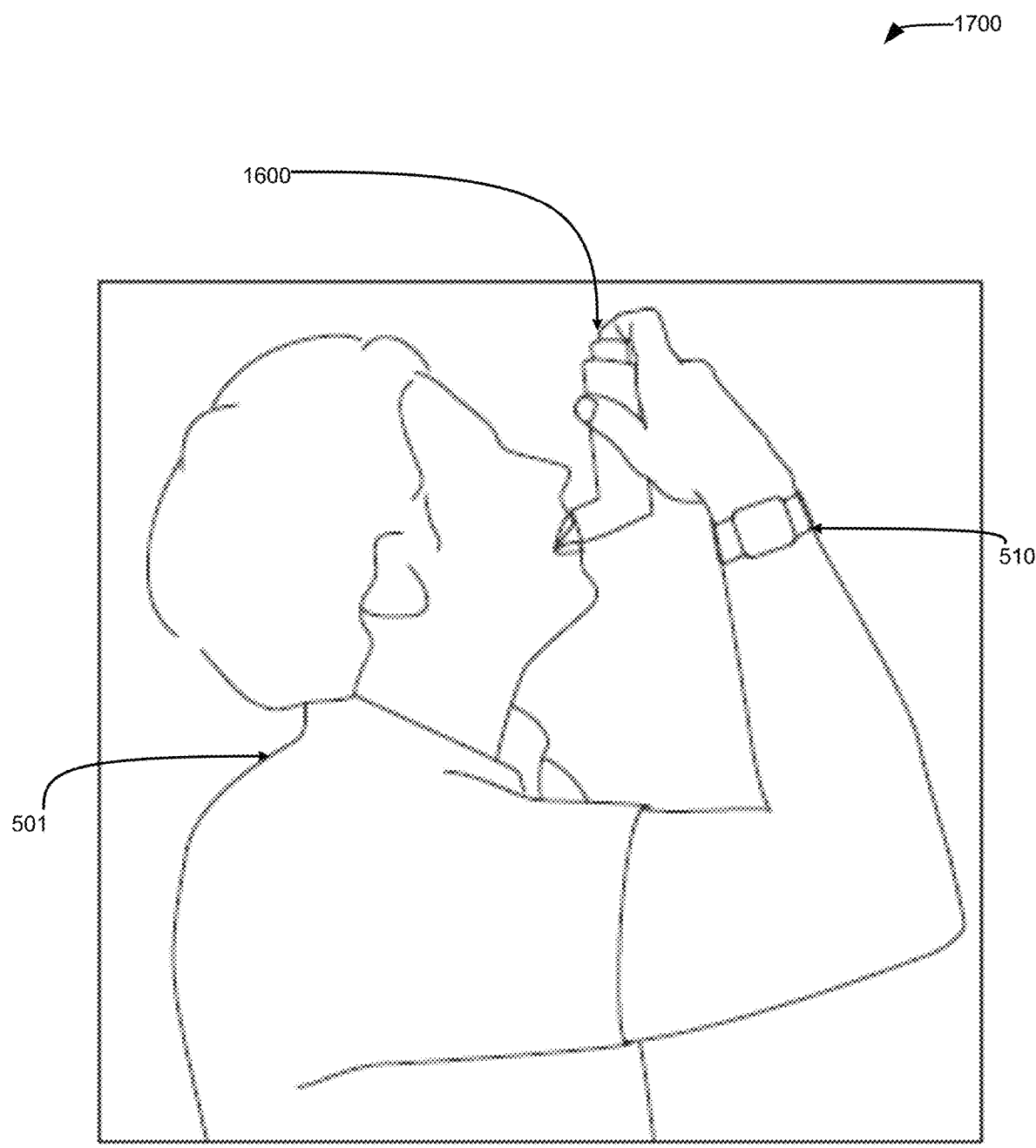

Referring to FIGS. 16-17, the illustrations depict a user 501 wearing a wearable computing device 510 seeking to use inhaler 1600 to inhale a prescription contained therein. From FIGS. 16-17, user 501 manipulates inhaler 1600 and carries it towards the mouth of user 501 and holds it in place before inhaling. Wearable computing device 510 is configured to detect the motion of the hand of user 501 when it moves inhaler 1600 from a resting position (in FIG. 16) to an active position (in FIG. 17) and when the user moves the top of inhaler 1600 to activate it for inhalation of the prescription pharmaceutical.

The motion model of user wearing the wearable device and be determined by sampling various users and the motions they use to ingest their medicines. The model can include various motion vectors for a type of user. The motion model can be set according to various characteristics of a user, e.g., whether the user is right-handed or left-handed. The various characteristics can assist in correctly identifying a dispensing motion of an ingesting a medicine motion. Another characteristic is whether the user wears the wearable device on an arms or wrist that (1) holds a medicine container or dispenser or (2) receives the medicine from the container or dispenser. The model can also be based on the type of medicine and how it is provided to the user. The model with various characteristics can be stored in a remote server, processed to identify the user, e.g., by the user characteristics, and then the motion vector profile for the user is pulled from the motion model and downloaded to the user device.

Various embodiments described herein relate to a patient dispensing a medication or a caregiver assisting a patient in taking a medication. These embodiments are not intended to train a medical professional to inject or otherwise perform a medical procedure on a patient. That is, the wearable device is intended in these described embodiments to be a layperson device and not intended for a physician or other medical professional.

The described use cases are presented for illustrative purposes. In other examples, other use cases of the systems and methods described herein may be provided by combining or adapting any of the described steps or any of the examples together.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

The foregoing description generally describes the wearable device in various embodiments as a watch, however, other wearables are within the scope of the present disclosure. Other examples of the wearable include bracelets or other personal accessories that are worn on a limb, and clothing. The graphical display can be secured in clothing, e.g., a sleeve, vest or flap of fabric.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information, but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave). The term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general-purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A wearable computing device for identifying gestures of prescription adherence, the wearable computing device comprising:
    a motion sensor configured to detect movement of a patient during performance of steps of a prescription by the patient; and
    one or more processors configured to determine that the wearable computing device is in a training mode and to direct the patient to perform the steps of the prescription during the training mode, the one or more processors configured to examine the movement of the patient that is detected by the motion sensor while the wearable computing device is in the training mode to define a gesture pattern model of the movement that is detected, the one or more processors configured to determine a separation distance between a medication container and the wearable computing device based on a proximity signal received from a communication interface associated with the medication container, the one or more processors configured to initiate selective monitoring for a motion pattern of the patient that matches the gesture pattern model based on the movement that is detected by the motion sensor while the wearable computing device is outside of the training mode and while the separation distance between the medication container and the wearable computing device is shorter than a distance threshold.

2. The wearable computing device of claim 1, wherein the one or more processors are configured to train the gesture pattern model based on the movement that is detected by the motion sensor while the wearable computing device is in the training mode to indicate that the patient is adhering to the prescription.

3. The wearable computing device of claim 1, wherein the one or more processors are configured to determine whether the gesture pattern model that is defined has been performed by the patient by analyzing the motion pattern of the patient that is monitored while the wearable computing device is outside of the training mode and while the separation distance between the medication container and the wearable computing device is shorter than the distance threshold.

4. The wearable computing device of claim 1, wherein the one or more processors are configured to update a prescription usage record responsive to determining that the gesture pattern model is performed by the patient.

5. The wearable computing device of claim 1, wherein the one or more processors are configured to update an inventory level of medication in the medication container associated with the prescription based on the movement that is detected by the motion sensor and to present the patient with a request to refill the prescription.

6. The wearable computing device of claim 1, wherein the one or more processors are configured to define the gesture pattern model to include one or more changes in an orientation and location of the wearable computing device as the patient moves the wearable computing device to different parts of a body of the patient during the training mode.

7. The wearable computing device of claim 6, wherein the one or more processors are configured to define the gesture pattern model to include the one or more changes in the orientation and location of the wearable computing device as the patient one or more of opens or closes the medication container.

8. A method for monitoring adherence of a patient to a prescription, the method comprising:
   detecting movement of the patient during performance of steps of the prescription by the patient using a motion sensor in a wearable computing device;
   determining that the wearable computing device is in a training mode;
   directing the patient to perform the steps of the prescription during the training mode;
   defining a gesture pattern model of the patient by examining the movement of the patient that is detected by the motion sensor while the wearable computing device is in the training mode;
   determining a separation distance between a medication container and the wearable computing device based on a proximity signal received from a communication interface associated with the medication container; and
   initiating selective monitoring for a motion pattern of the patient that matches the gesture pattern model based on the movement that is detected by the motion sensor while the wearable computing device is outside of the training mode and while the separation distance between the medication container and the wearable computing device is shorter than a distance threshold.

9. The method of claim 8, wherein the gesture pattern model is trained based on the movement that is detected by the motion sensor while the wearable computing device is in the training mode to indicate that the patient is adhering to the prescription.

10. The method of claim 8, further comprising:
    determining whether the gesture pattern model that is defined has been performed by the patient by analyzing the motion pattern of the patient that is monitored while the wearable computing device is outside of the training mode and while the separation distance between the medication container and the wearable computing device is shorter than the distance threshold.

11. The method of claim 8, further comprising:
    updating a prescription usage record responsive to determining that the gesture pattern model is performed by the patient.

12. The method of claim 8, further comprising:
    updating an inventory level of medication in the medication container associated with the prescription based on the movement that is detected by the motion sensor; and
    presenting the patient with a request to refill the prescription.

13. The method of claim 8, wherein the gesture pattern model is defined to include one or more changes in an orientation and location of the wearable computing device as the patient moves the wearable computing device to different parts of a body of the patient during the training mode.

14. The method of claim 13, wherein the gesture pattern model is defined to include the one or more changes in the orientation and location of the wearable computing device as the patient one or more of opens or closes the medication container.

15. A wearable computing device comprising:
    one or more processors configured to determine that the wearable computing device is in a training mode and to direct a patient to perform steps of a prescription during the training mode,
    the one or more processors configured to define a gesture pattern model of patient movement that is detected by a motion sensor while the wearable computing device is in the training mode,
    the one or more processors configured to determine a separation distance between a medication container and the wearable computing device based on a proximity signal received from a communication interface associated with the medication container,
    the one or more processors configured to determine that the wearable computing device is within a threshold distance of a medication container and to initiate selective monitoring for a motion pattern of the patient that matches the gesture pattern model based on the patient movement that is detected by the motion sensor while the wearable computing device is outside of the training mode and while the wearable computing device is within the threshold distance of the medication container.

16. The wearable computing device of claim 15, wherein the one or more processors are configured to train the gesture pattern model based on the patient movement that is detected by the motion sensor while the wearable computing device is in the training mode to indicate that the patient is adhering to the prescription.

17. The wearable computing device of claim 15, wherein the one or more processors are configured to determine whether the gesture pattern model that is defined has been performed by the patient by analyzing the motion pattern of the patient that is monitored while the wearable computing device is outside of the training mode and while the wearable computing device is within the threshold distance of the medication container and the wearable computing device is shorter than the threshold distance.

18. The wearable computing device of claim 15, wherein the one or more processors are configured to update a prescription usage record responsive to determining that the gesture pattern model is performed by the patient.

19. The wearable computing device of claim 15, wherein the one or more processors are configured to update an inventory level of medication in the medication container associated with the prescription based on the patient movement that is detected by the motion sensor and to present the patient with a request to refill the prescription.

20. The wearable computing device of claim 15, wherein the one or more processors are configured to define the gesture pattern model to include one or more changes in an orientation and location of the wearable computing device as the patient moves the wearable computing device to different parts of a body of the patient during the training mode.

* * * * *